United States Patent
Catlett

[19]

[11] Patent Number: 6,155,967
[45] Date of Patent: Dec. 5, 2000

[54] COSMETIC AND THERAPEUTIC MASK ASSEMBLY WITH ACCESSIBLE AND POSITIONABLE MAGNETIC POCKET MEANS

[76] Inventor: James A. Catlett, 2712 Ore Band Rd., Pigeon Forge, Tenn. 37863

[21] Appl. No.: 09/251,794

[22] Filed: Feb. 17, 1999

[51] Int. Cl.[7] .................................................. A61N 1/00
[52] U.S. Cl. ..................... 600/15; 128/857; 606/204.35
[58] Field of Search .................................. 128/845, 846, 128/857, 858; 600/9–15; 606/204.35

[56] References Cited

U.S. PATENT DOCUMENTS

| | | | |
|---|---|---|---|
| 1,006,415 | 10/1911 | Stubling | 600/15 |
| 5,706,828 | 1/1998 | Shiota | 128/857 |
| 5,738,624 | 4/1998 | Zublotsky | 600/15 |

FOREIGN PATENT DOCUMENTS

| | | | |
|---|---|---|---|
| 2575926 | 7/1986 | France | 600/15 |
| 2583292 | 12/1986 | France | 600/15 |

*Primary Examiner*—Michael A. Brown
*Attorney, Agent, or Firm*—M. Alex Brown, Patent Attorney

[57] ABSTRACT

A cosmetic and therapeutic mask assembly with an accessible and positionable magnetic pocket system is disclosed for use in interaction with and treatment of a face, head or other body area of a human or animal treatment subject. The invention is provided with an elastic support pattern of one or more layers which is provided with an integral or multi-ported space designed to fit adjacently to sense organs or other body areas, or skin or tissue. A number of subassemblies having accessible fluted pivot pockets, each having access grooves, arranged in series or by virtue of other configurations, are positioned close to the perimeter of the pivot space and affixed to the support pattern. A number of magnets, each having positive and negative poles, are respectively mounted in the pivot pockets where they can be pivoted and positioned by contact through the respective access grooves, or prepositioned before installation; to create magnetic pairings of adjacent pocketed magnets, to transmit and communicate a magnetic differential and field producing a magnetic effect and resulting attraction and repulsion forces, through or traveling through the support pattern to an adjoining treatment area. The invention is further provided with an attachment strap or belt or like structure for securing and installing the mask assembly of the invention functionally snugly in relation to a treatment area.

26 Claims, 25 Drawing Sheets

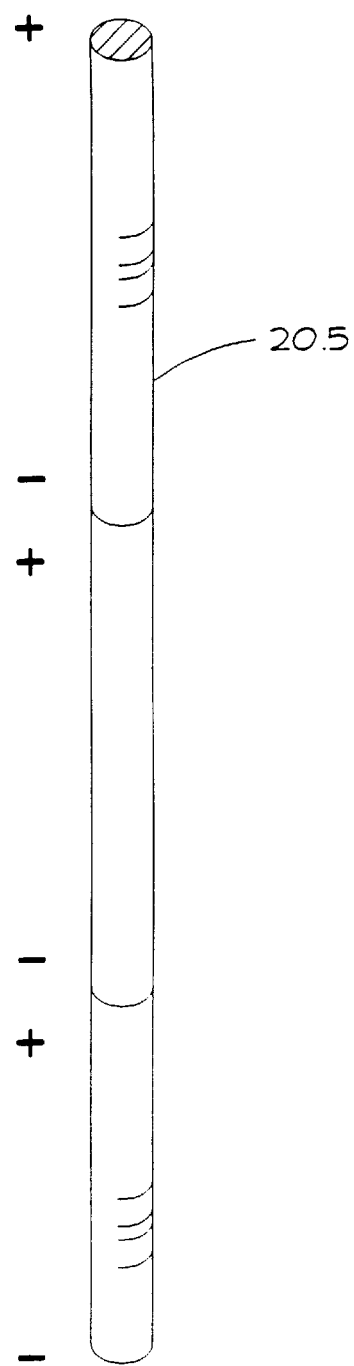
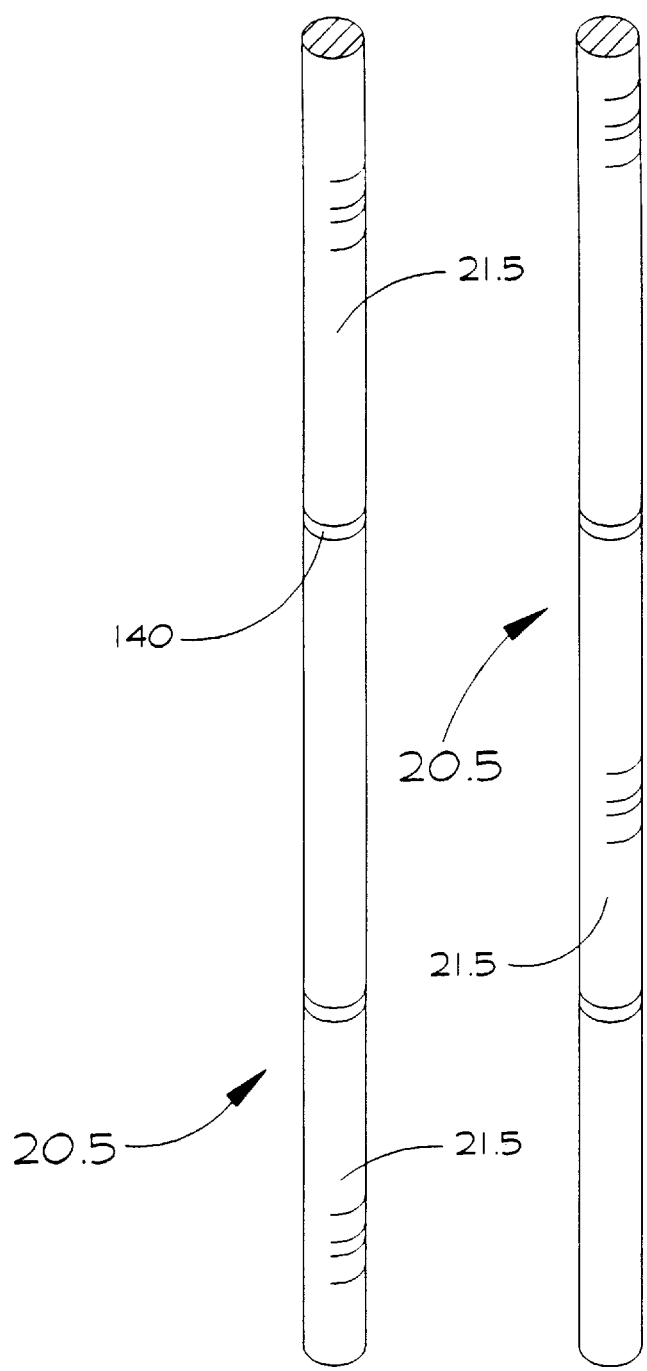
FIG. 6E
FIG. 6F

COSMETIC AND THERAPEUTIC MASK ASSEMBLY WITH ACCESSIBLE AND POSITIONABLE MAGNETIC POCKET MEANS

FIELD OF THE INVENTION

The present invention relates to a mask device having magnets attached to it for use in relation a human's face for cosmetic and health purposes.

BACKGROUND INFORMATION

Although no references were found specifically relating to the present invention, those references typical of other marginally related prior art found in the process of a patent search include United States patents to Rodriquez, U.S. Pat. No. 5,295,494; Morenings, U.S. Pat. No. 4,957,480; Rooney, U.S. Pat. No. 4,189,141; Ruscitti et al., Des. 380,556; Ruscitti et al., Des. 359,362; and Golay, U.S. Pat. No. 4,475,249.

Additionally, the published literature has made reference in recent years to the health benefits of magnetic or biomagnetic treatments to compromised or diseased areas in general.

Specifically, the Rodriquez '494 patent reference teaches a support for a therapeutical magnet, to be strapped by belt and buckle to the body for therapeutic treatment; and a number of similar envelope-type support structures have been utilized to simply place, or strap, one magnet, or unitary magnet, flush and non-movably against the body for health benefits thereof.

The Morenings '480 reference teaches a method of facial toning, based on stimulation of motor nerves by application of predetermined galvanic currents, by means of continually moistened electrode tips.

Rooney '141 sets forth a mask for exercising facial muscles, by virtue of massive lead or omnium weights enclosed in pockets secured inside the mask, for positioning at brow, temple, cheek, nose and chin portions of a person. No magnetic differential, positioning or effect is taught in Rooney.

The Ruscitti '556 and '362 teach of way of design ornamentation a combination magnetic health and beauty mask, each having what appears to be positionally fixed, non-pivotal and non-moving magnetic members attached to the respective masks. Additionally, Ruscitti does not teach any accessible pocket or other means for varying polarity and magnetic differential; or replacement or variance of magnetic component elements to achieve therapeutic and health purposes.

Golay '249 simply teaches a markedly unrelated, air cleaning magnetic attachment for a welder's face mask.

Additionally, other prior art references have generally addressed other magnetic treatment of human tissue. Examples of this art includes McLeod, U.S. Pat. No. 4,993,413; Markoll, U.S. Pat. No. 5,665,049; and Graston, U.S. Pat. No. 5,707,346. McLeod relates to a method and apparatus for inducing a current and voltage in living tissue, with a device and means substantially distinguishable from the present invention. Markoll relates to a treatment of acute diseases as caused by the sports-type injuries of the musculoskeletal system (excluding fractures) with magnetic field therapy, utilizing a large annular coil surrounding the diseased organ; a coil which is energized by a pure DC voltage having a rectangular wave form pulsing at the rate of 1–30 CPS. And Graston relates to a system and method for performing soft tissue massage therapy, which utilizes a contoured tool connected to a source of electrical current for providing electrical stimulation to an impaired area. Each of these references is substantially different structurally and functionally from the present invention.

None of the references found in the prior art specifically illustrate or disclose the improved cosmetic and therapeutic mask assembly of the present invention. Nor is the present invention obvious in view of any of the prior art references listed. In addition, all of the relevant prior art heretofore known suffer from a number of disadvantages.

None of the prior art devices or method of use address accessible magnet bearing pocket members on a mask pattern for the purpose of moving parts of the mask by magnetic differential patterns to cause a cosmetic or health benefit from such a magnetic differential, along with the included repulsion (pushing) and attraction (pulling), as a part thereof, to cause a magnetically activated movement of adjacent skin and muscle tissue of a treatment subject.

Additionally, none of the prior art devices provide the structural and functional ability to utilize cylindrical configured magnets; nor do they provide the ability to utilize such magnets in flexible and multi-sectioned and jointed embodiments, to achieve greater flexible access and magnetic effect of adjacent or proximally located head, face or muzzle skin, nerve and muscle areas of a human or animal.

Additional limitations of the prior art also include flexibly adopt and magnetically serve, by virtue of repulsion and attraction, many different areas of the face or head of a treatment subject, including areas proximal or adjacent to eye, ear, nose, mouth and chin or muzzle areas of a treatment subject.

Also, other devices do not afford the user the ability to manually massage the selected area and also create respective positive-positive, negative-negative and positive-negative, magnetic pairings or couplings; to affect attracting/repelling energy, and circulation to adjacent areas of the head and face.

Other devices do not address or teach pivotable mounting while permitting accessible pocket stabilization of a plurality or number of flexible magnet elements, to prevent their collecting in a unitary group or mass, while also permitting access, positional movement, and replacement of different magnetic component embodiments (such as multi-sectioned and jointed, flexible magnets).

Also, the prior art devices do not adequately address the layering and fabric quality characteristics for best affecting transmittal and positioning of magnetic forces.

Further, none of the prior art devices or methods properly address the structural and functional ability to pull face or head tissue upward and outward by virtue of flexible or biasing force vectors of a mask pattern, while also and contemporaneously affecting through multiple and positionable magnetic component members a "pulling" together and "pushing" apart of skin and adjacent tissue; thus creating a movable physical and bio-magnetic effect, to address wrinkles, aging or pathology.

These and other disadvantages, structurally and functionally, of the prior art, will become apparent in reviewing the remainder of the present specification, claims and drawings.

Accordingly, it is an object of the present invention to provide a mask-like pattern which affords the user or treatment recipient the ability to manually pivot and position rollable magnet components to, both, massage a selected treatment area, and create, by so positioning, a magnetic differential through respective pairings of positive-positive, negative-negative and positive-negative poles of individual magnets; to affect respective attraction and repulsion energy, and circulation-effect and treatment to areas of the head or face, or other chosen tissue treatment areas of the body of a human or animal. A further related object affords the ability in utilizing the present invention, to create such a magnetic differential through interchangeable, segmented (and flexible jointed) or integrally constructed flexible pivotable magnet members which have positive and negative poles by virtue, sturcturally, of lengthwise orientation or widthwise orientation, positionally; allowing for great diversity in affecting magnetic treatment of a skin and tissue area.

It is a further object of the invention to provide a flexible device providing pivotable mounted, accessible, and fluted pocket series stabilization of a number of flexible magnet members or components, preventing their collection in a mass, integral or unitary group, while still providing access and replacement of individual or respective magnet components, and flexible positioning for providing treatment to body areas.

It is yet a further object of the present invention to provide a masked-pattern device and assembly having mesh fabric layering and fabric quality, to facilitate transmittal of magnetic forces (magnetic differential) and to facilitate flexible access to areas of the face, head, and body selected for treatment, therapy of massage.

It is a further object of the invention to provide a pattern assembly which supports and positions a plurality or number of magnetically interacting magnetic components, grouped respectively in series-positioned pockets, with each magnet element or component being flexible, powerful and variable, through widthwise or lengthwise magnetic poles, for creation of a magnetic differential, by virtue of respective magnetic pairings of positive-positive, negative-negative, and positive-negative poles on respective pairings of magnet members; brought about by flexible access and positioning of individually pivotally pocketed magnets.

It is also an object of the present invention to provide a flexible and positionable magnet means which also provides the ability to utilize face or body cream, or therapeutic/ medical fluids, while not detracting from the interacting magnetic effect of the inventions's respective plurality of movable magnet components, and their treatment effect.

It is yet a further object of the invention to provide a face-mask assembly, as well as other assemblies so constructed for other body locations, having the structural and functional ability to pull face, head or body overlying tissue upward and outward by virtue of flexible or biasing force vectors of the invention's main support pattern, while also and contemporaneously affecting through multiple and positionable magnetic component members a "pulling" together and "pushing" apart of skin and adjacent tissue; thus creating a movable physical and biomagnetic effect, to address existing wrinkles and/or pathology.

Further objects of the present invention also are set forth in providing a face mask assembly, where magnet components movably supported on the assembly, can be interchanged and replaced; and where all such magnets can be slideably and replaceably removed from the assembly so that it can be washed, dry-cleaned, laundered or otherwise cleaned when needed; or when lotions creams, or health or therapeutic fluids, utilizable in combination with the invention (and its function), are so utilized.

Yet a further object is achieved by the invention in providing a masked assembly which pivotally supports interacting magnetic components in an area very close to, or generally, positionally flush, against the skin or outerlying tissue of a treatment recipient; so that loss of magnetic differential (or poled magnetic) power (in accordance with the principal of loss of such magnetic power being a function of the treatment or positioned distance, 'squared') is efficiently minimized.

It will, therefore, be understood that substantial and distinguishable structural and functional advantages are realized in the present invention over the prior art devices; and that the present invention's novel structure, diverse utility, broad functional applications serve as important bases of novelty and distinction in this regard.

SUMMARY OF THE INVENTION

The foregoing and other objects of the invention can be achieved with the present invention, device, assembly and functional method of use; which is a therapeutic assembly for masked positional orientation and magnetic treatment, in interaction with a face or head of a treatment recipient. The therapeutic assembly is provided with an elastic support pattern which has and defines at least one elastic pivot hole, positioned to align proximally, when in an installed position for treatment use, with a sensing structure-organ of a face or head. The elastic support pattern is provided with means for so securing the elastic support pattern in an installed position. The therapeutic assembly is further provided with a plurality of magnet components having, when so positioned, a magnetic differential thereof to attract and repel in relation to one another; and is also provided with at least one pocket subassembly attached to the elastic support pattern, adjacent positionally to the elastic pivot hole. The pocket subassembly, and each one thereof, is provided with means for removably mounting and pivotally positioning each of the plurality of magnet components in relation to one another for selectively engaging the magnetic differential thereof to attract and repel. Each of the plurality of magnet components is mounted in each pocket subassembly and selectively positioned, when so mounted, to, thereby, engage the magnetic differential thereof to attract and repel, to correspondingly transmit a resulting pulling and pushing force, respectively, through the elastic support pattern to areas of the face or head of a treatment recipient with which the therapeutic assembly interacts.

BRIEF DESCRIPTION OF THE DRAWINGS

FIG. 1 is a side perspective view of one preferred embodiment of the novel improved cosmetic and therapeutic mask assembly of the present invention, also showing in general detail the outline of a face area of a treatment recipient with which the present invention interacts with.

FIG. 6E is a front perspective, illustrating one respective magnet component utilized in the invention, where the magnetic component is jointed in sub-sections, and magnetic differential is achieved by lengthwise positional orientation thereof.

FIG. 6F is a front perspective of a group of respective magnet components utilized in the invention, illustrating flexible joint members, separating the sub-sections of each respective magnet member.

Figure 1:
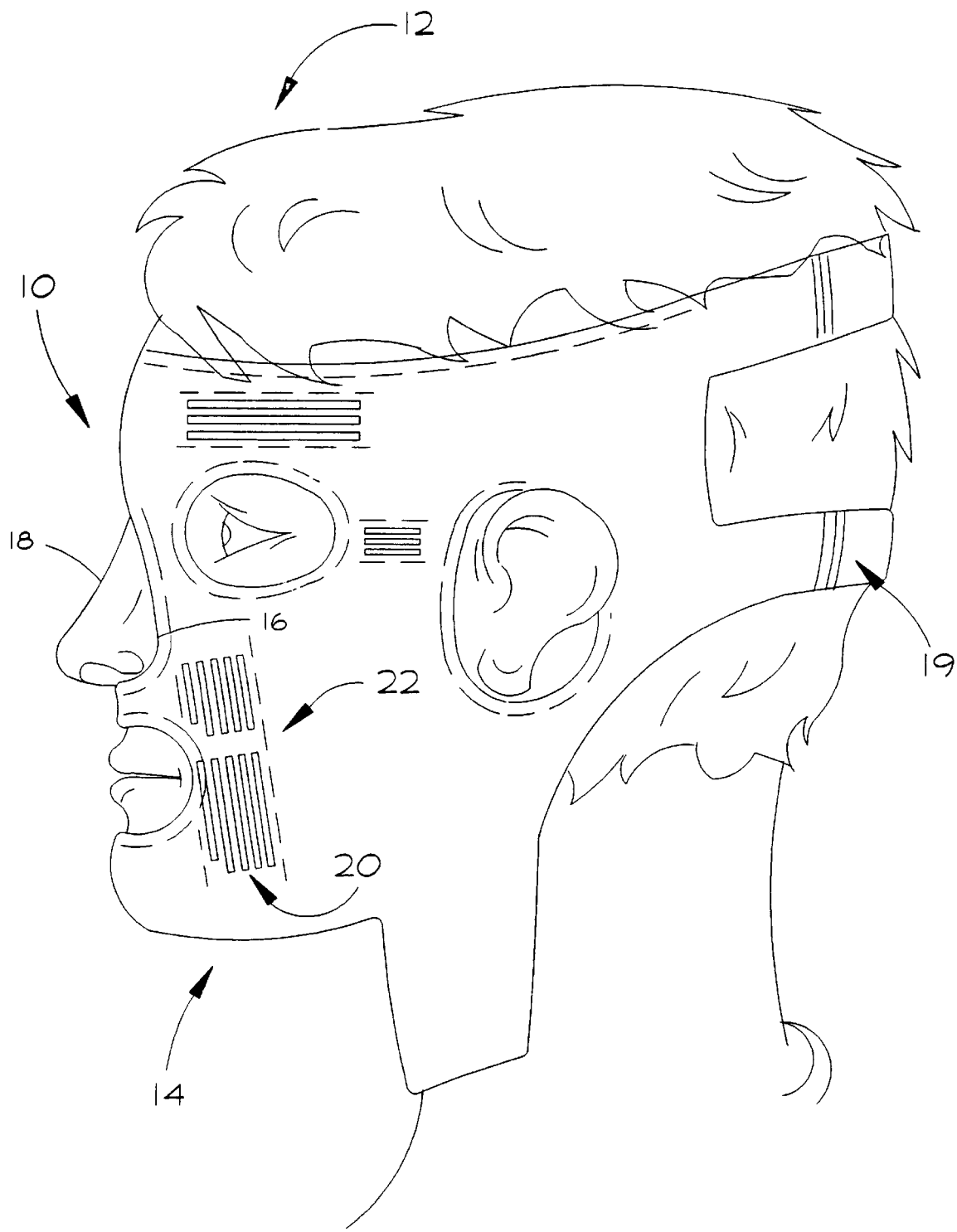

REFERENCE NUMBERS IN DRAWINGS 10 mask assembly or mask of present invention
12 face/head area of treatment recipient/subject with which present invention interacts
14 elastic support pattern
16 elastic pivot hole
18 sensing structure organ of treatment subject
19 strap means
20 magnet component(s)
22 pocket subassembly
24 pocketed means of (22)
26 first elastic pivot hole of (14)
26A first lateral portion of (26)
26B second lateral portion of (26)
26C anterior portion of (26)
26D posterior portion of (26)
36 second elastic pivot hole of (14)
36A lateral portion of (36)
36B medial portion of (36)
36C anterior portion of (36)
36D posterior portion of (36)
46 third elastic pivot hole of (14)
46A lateral portion of (46)
46B medial portion of (46)
46C anterior portion of (46)
46D posterior portion of (460
56 fourth elastic pivot hole
56A first lateral portion of (56)
56B second lateral portion of (56)
56C anterior portion of (56)
56D posterior portion of (56)

Figure 22:
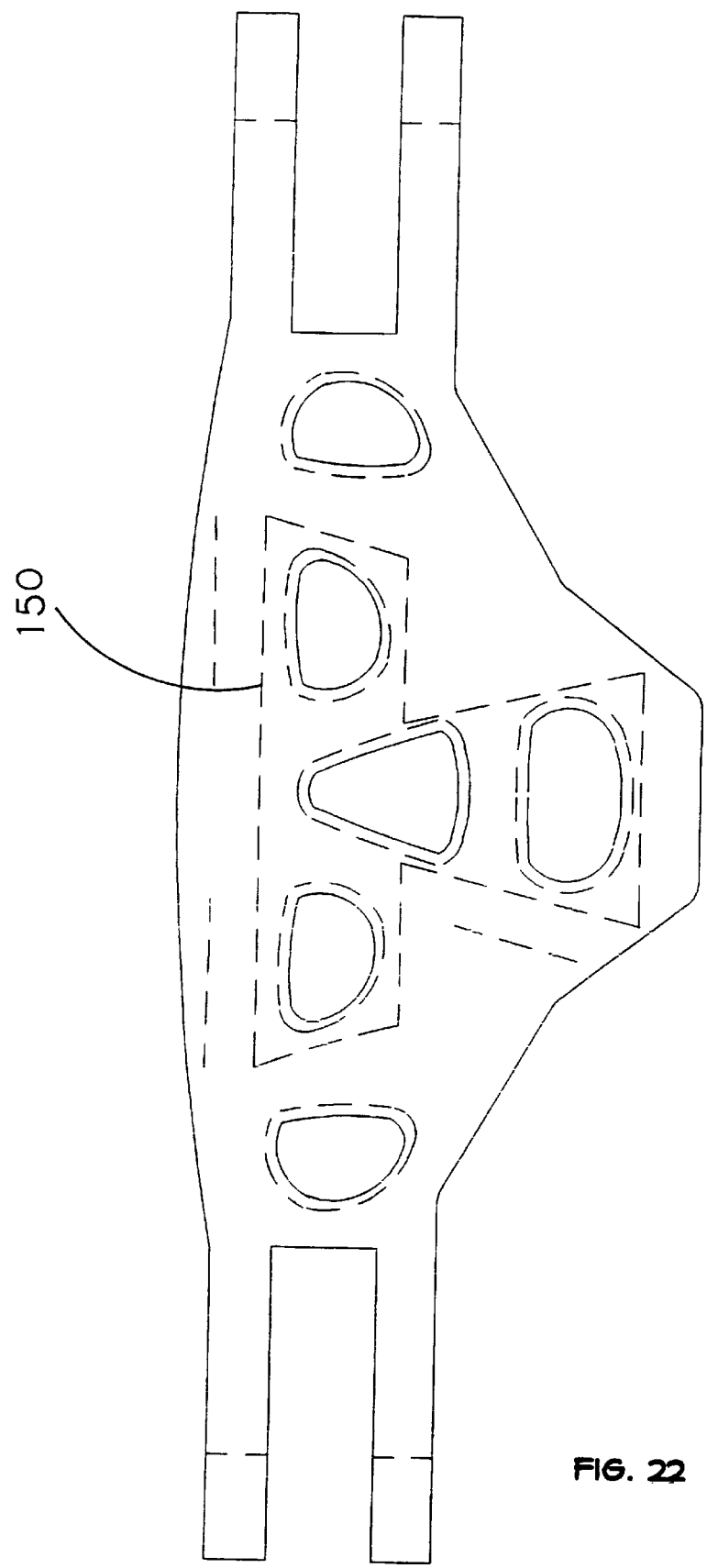
FIG. 22 is a front perspective general pattern view of another embodiment of the elastic support pattern of the present invention, showing in general detail where eye, nose and mouth holes would have been; and, by broken lines, where the elastic pivot hole in this embodiment is preferably located.
Figure 23:
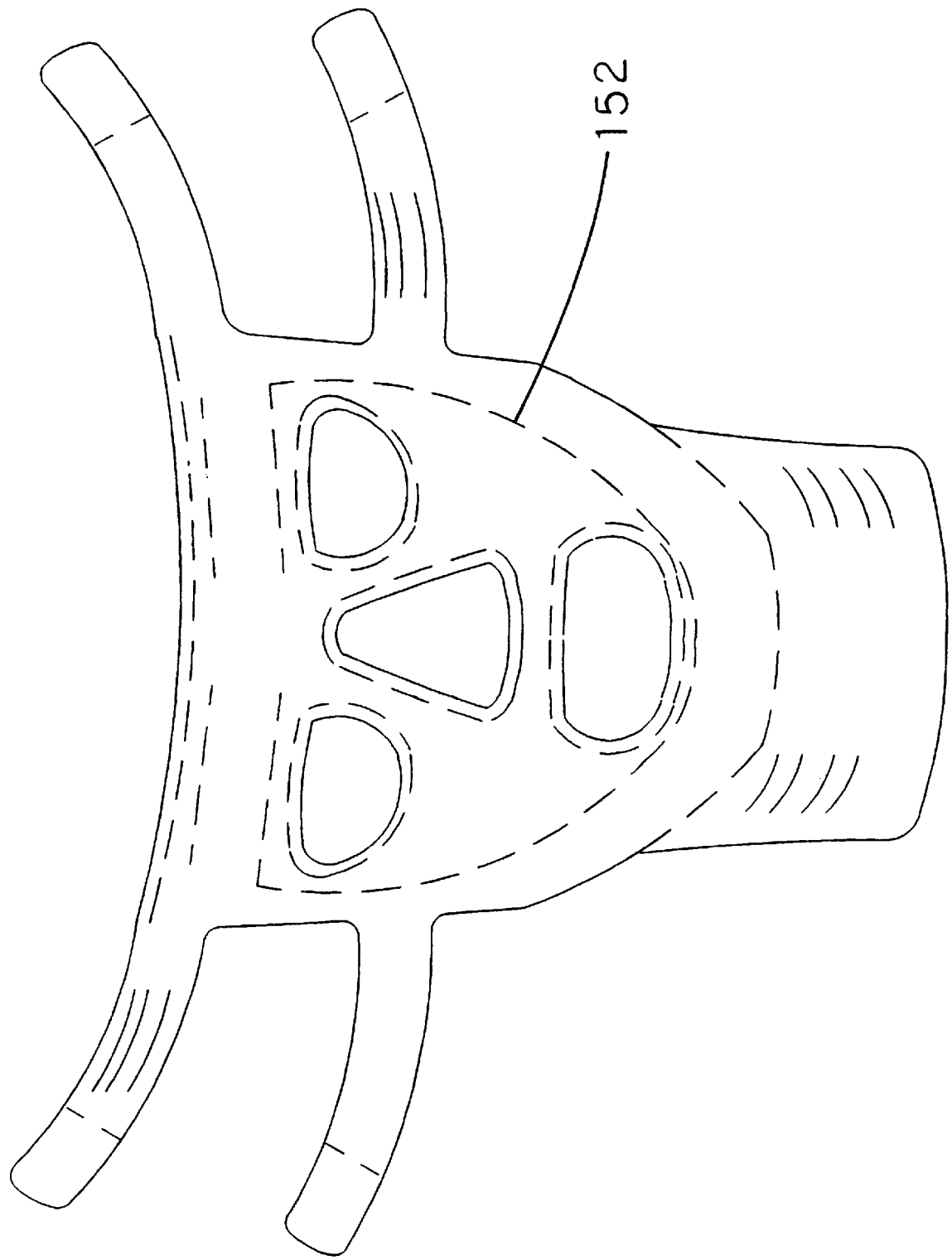
FIG. 23 is a front perspective general pattern view of the elastic support pattern, showing in general detail where the eye, nose and mouth holes would have been; and, by broken lines, where the elastic pivot hole in this further embodiment is located.
Figure 24:
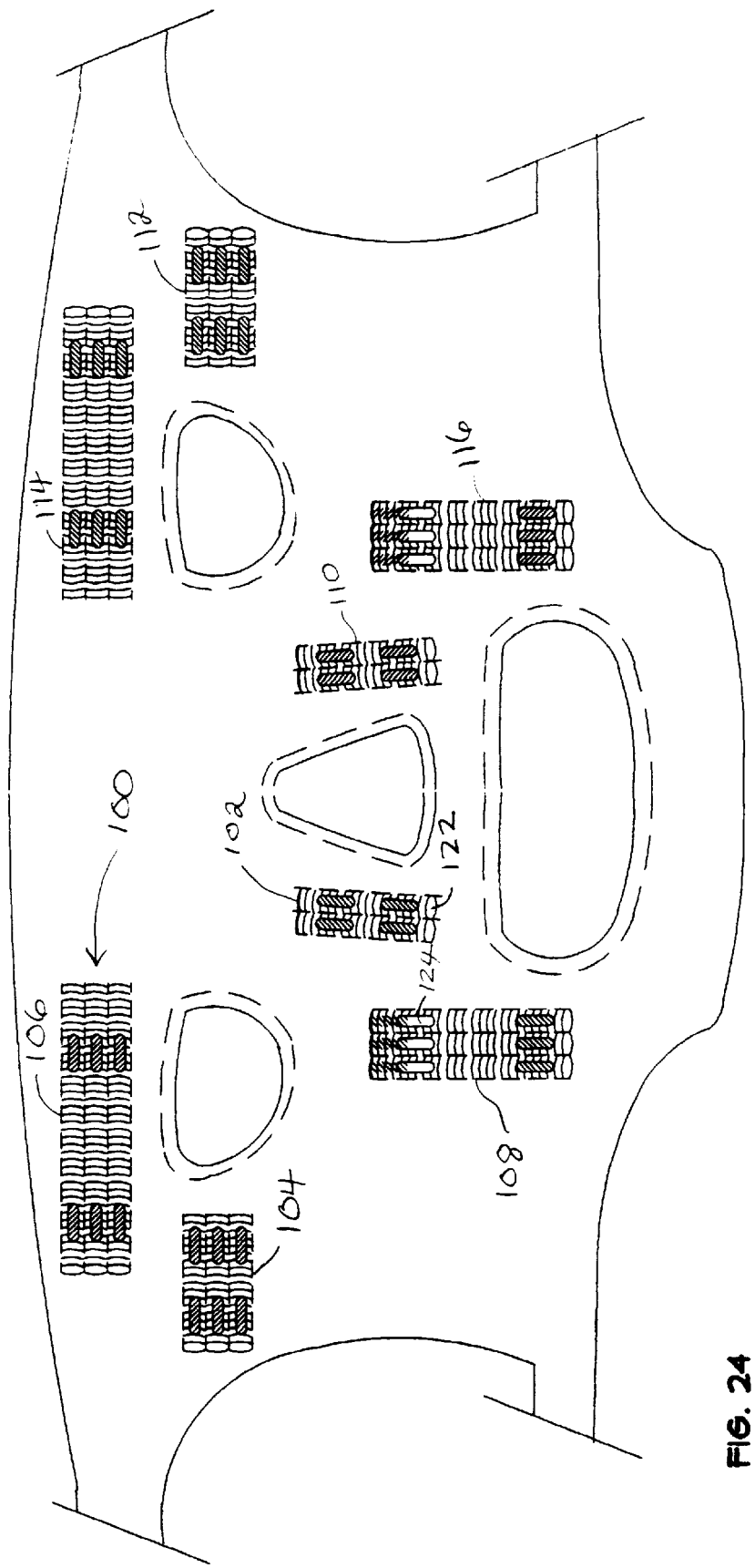
FIG. 24 is a front plan view of an embodiment related to that of FIGS. 16 and 21.
Figure 25:
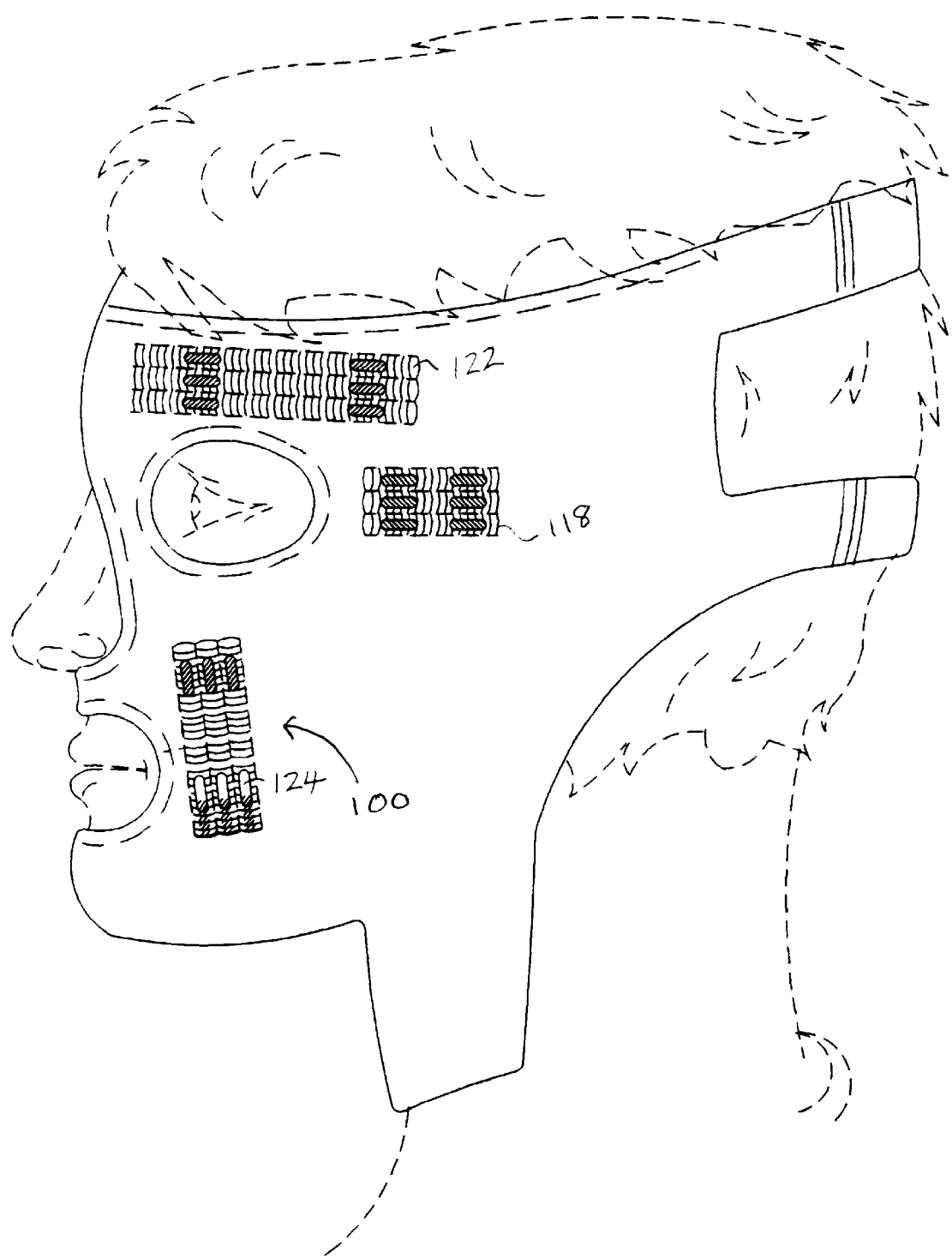
FIG. 25 is a left side perspective view of the embodiment of FIG. 24, showing a human head and face area, an example of a treatment subject with which the invention interacts, in general detail.
Figure 26:
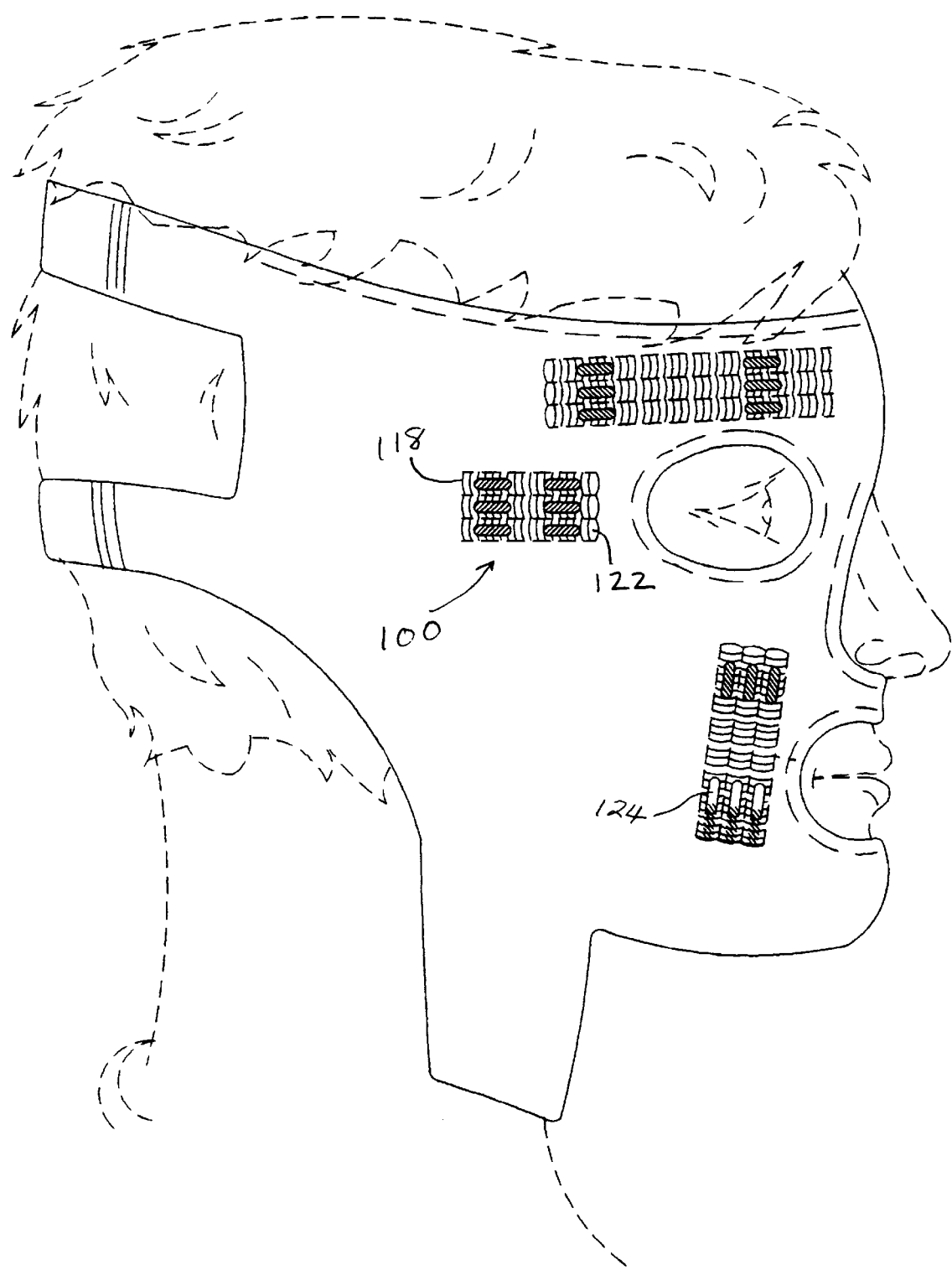
FIG. 26 is a right side perspective of the embodiment of FIG. 24, showing a human head and face area, by example of a treatment subject, with which the invention interacts, in general detail.
Figure 27:
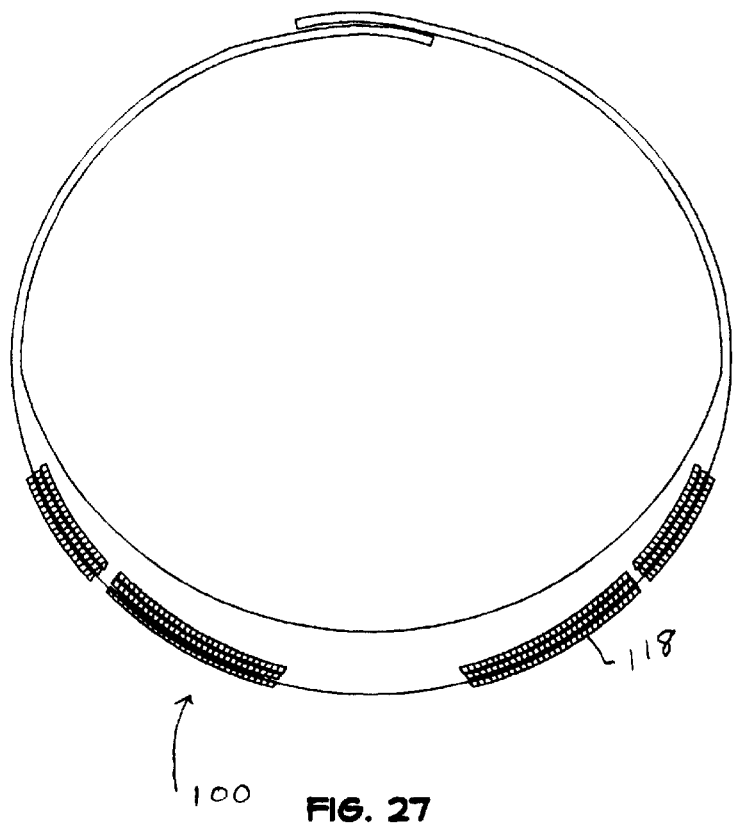
FIG. 27 is a reduced scale top perspective of the embodiment of FIG. 24.
Figure 28:
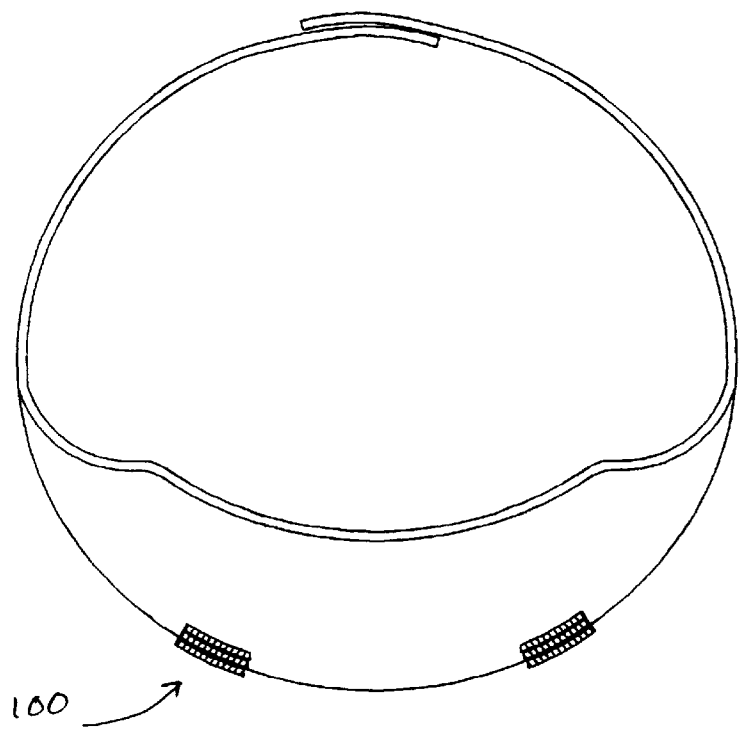
FIG. 28 is a reduced scale bottom perspective of the embodiment of FIG. 24.

66 collar member of (24)
20.5 multi-sectioned or jointed magnet
70 first surface of (14)
72 second surface of (14)
74 first end portion of (14)
76 second end portion of (14)
78 first side section of (14)
80 second side section of (14)
82 first belt member of (19)
84 second belt member of (19)
86 first end (cylindrical magnet)
88 second end (cylindrical magnet)
90 circumferential surface (cylindrical magnet)
92 first cross-sectional surface (cylindrical magnet)
94 second cross-sectional portion (cylindrical magnet)
96 lengthwise axis (cylindrical magnet)
97 notched magnet member
97.5 positioning groove
98 collar lumen
100 pocketed series assembly means
102 first elastic-biasing pocket subassembly
104 second elastic-biasing pocket subassembly
106 third elastic-biasing pocket subassembly
108 fourth elastic-biasing pocket subassembly
110 fifth elastic-biasing pocket subassembly
112 sixth elastic-biasing pocket subassembly
114 seventh elastic-biasing pocket subassembly
116 eighth elastic-biasing pocket subassembly
118 fluted pivot pocket
120 installation channel of (118)
122 installation opening of (118)
124 rounded access groove
126 second layer of (14)
128 first layer of (14) (of such an embodiment)
132 cross-radial biasing elements of (118)
134 lengthwise biasing fabriced elements of (118)
140 magnet joint meniscus element of (20.5)
21.5 jointed magnet subportions
148 stitching (of pocket 118)
150 trapezoidal configuration and embodiment of (16)(FIG. 22)
152 parabolic, or parabola-like, configuration and embodiment of (16) (FIG. 23)

DETAILED DESCRIPTION OF THE PREFERRED EMBODIMENTS OF THE INVENTION

The following description of the preferred embodiments of the concepts and teaching of this present invention is made in reference to the accompanying drawing figures which constitute preselected illustrated examples of the structural and functional elements of the invention, among many other examples existing within the scope and spirit of the invention.

Referring now to the drawings, FIGS. 1, 2, 4, 7, 8, 9, 12, 13, 14, 16 and 21, thereof, there is shown a magnetic, cosmetic and therapeutic mask assembly 10, of the present invention, referred to herein as the masked assembly or mask, 10.

The mask 10 is utilized in interaction with a face, head, muzzle, or other outer-lying body tissue area. The face/head area 12 of a human is shown by example in the drawings, in general detail; and does not constitute part of the invention per se, but rather an example of a human or animal with which the invention can be used in interaction.

The mask assembly 10 is provided with an elastic support pattern 14 which has at least one elastic pivot hole 16. In a preferred embodiment of the invention, each elastic pivot hole 16 is positioned on the support pattern 14, to align positionally close, or proximal, to a sensing structure-organ 18 of a face/head 12, such as eyes, nose, muzzle or mouth, when the support pattern 14 is in an installed position for treatment use, or installed on a treatment recipient, which can be an animal or human treatment subject.

The pattern 14 is further provided with strap means 19 for securing the pattern 14, in an installed position, as illustrated by example, and otherwise, to the face/head area 12 of a treatment subject or recipient. It will be understood that the strap means 19 can take the form of any of a diverse number, or embodiments, of adjustable closures, velcro-close, belted, banded, fabriced, wired, and other types of coupling or securing members, which wrap around or secure, or adhere; the pattern 14 to the face/head area 12, or other body area selected for treatment. In this regard, it will be understood that the present invention, though preferably utilized in orientation with a face/head area 12, can also be used in relation to other areas of outer-lying skin and tissue, such as shoulder, knee, other jointed body areas, and other body areas.

Additionally, the elastic support pattern 14 is preferably fabricated from a flexible, meshed, magnetically neutral or conducting fabric or material constructive material such as power net, stretch Lyera lining, elastic mesh material; or other mesh material having respective band sub-fabric components to place respective biasing pressure on skin and/or underlying tissue; or other stretchable, unitary fabric material, compatible or user-friendly with respect to magnetic components or magnets.

Figure 19:
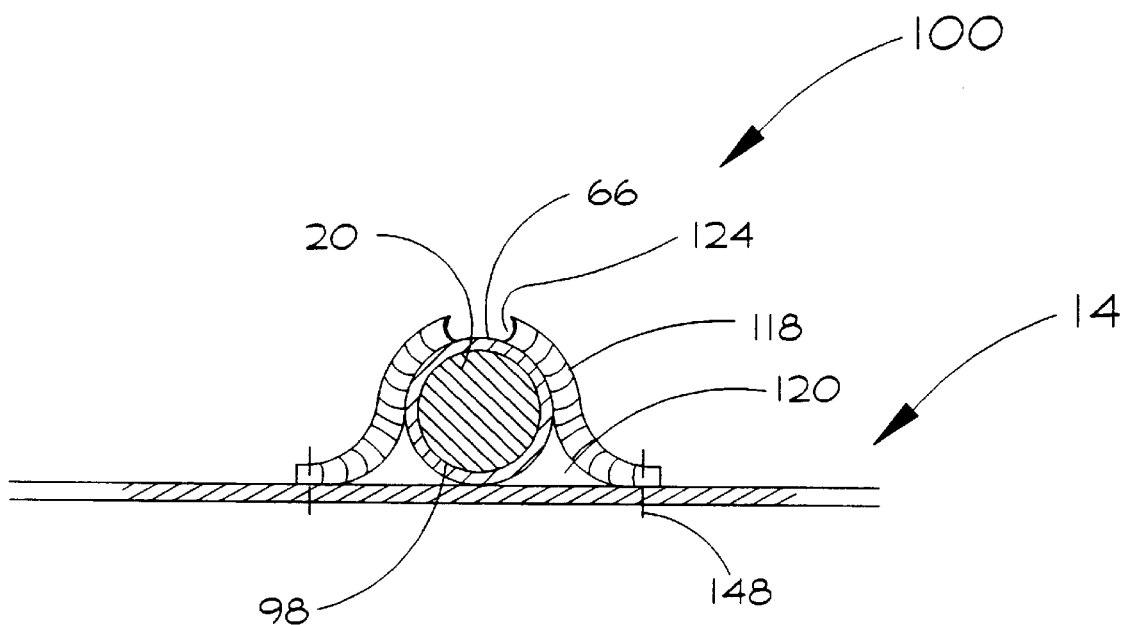
FIG. 19 is an enlarged cross-sectional view of FIG. 16, along line-19, thereof.
Figure 16:
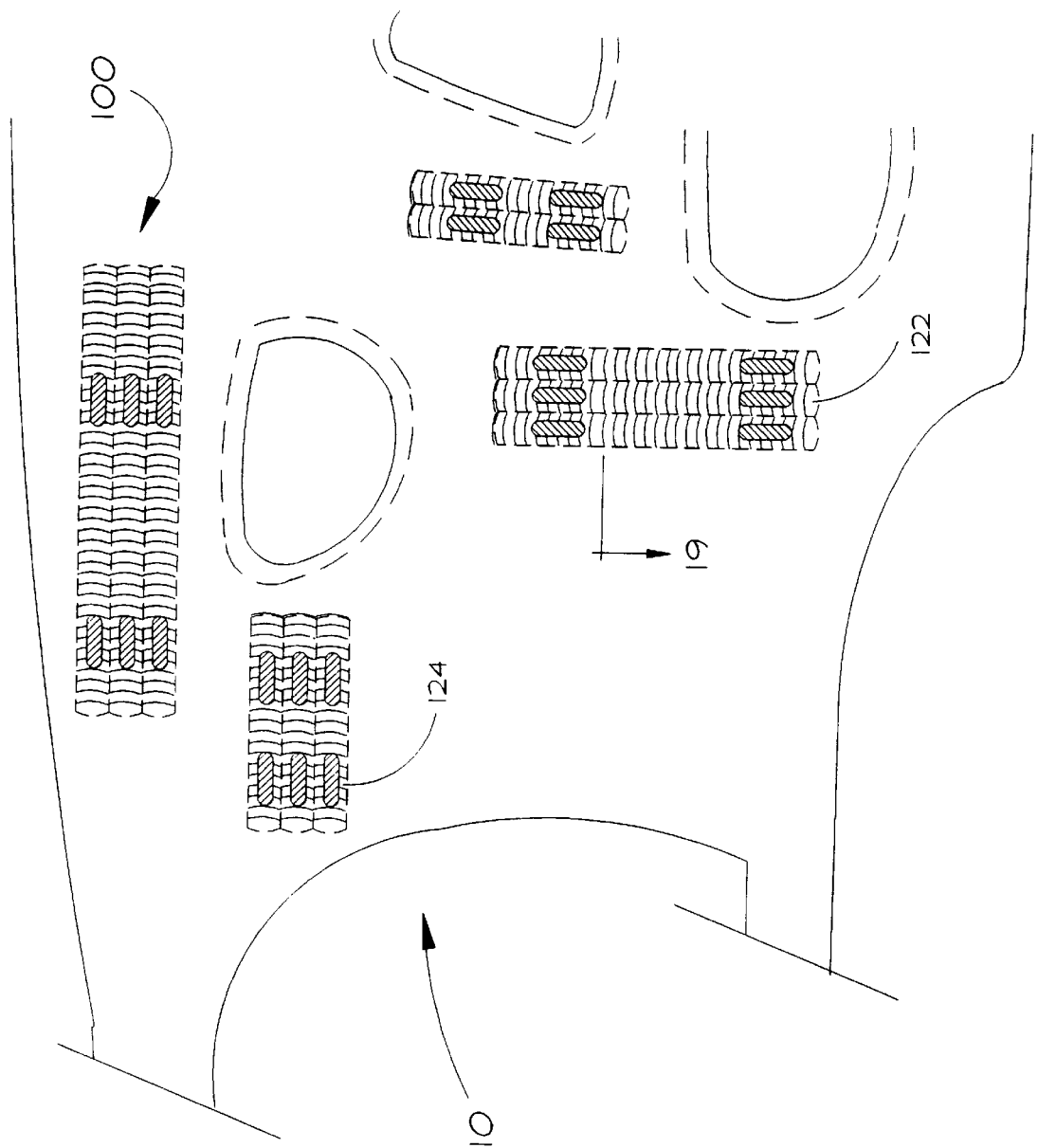
FIG. 16 is a partial front perspective of another embodiment of the invention.
Figure 20:
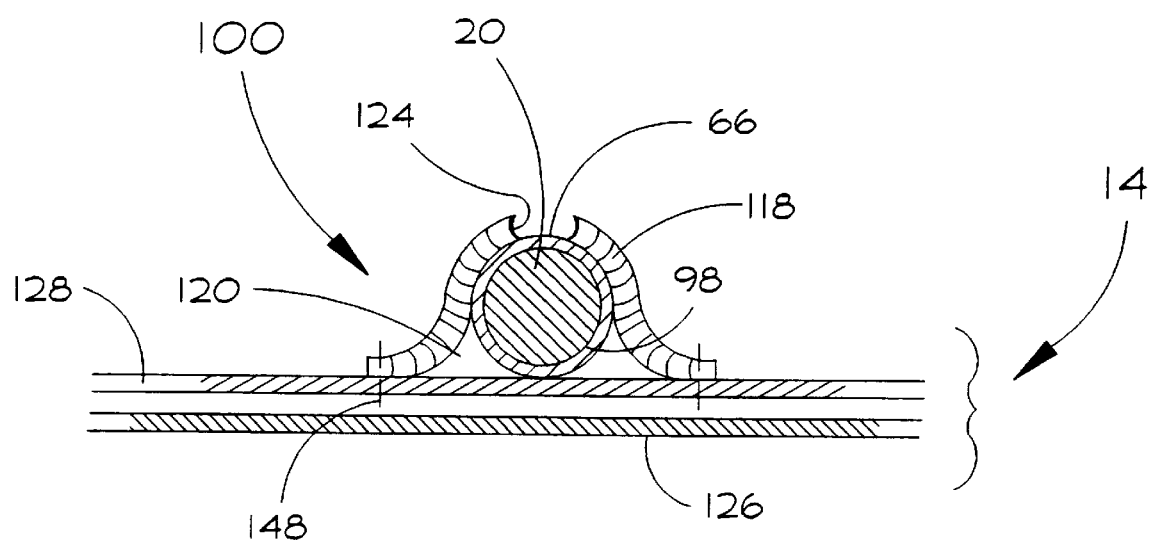
FIG. 20 is a similar view to that of FIG. 19, showing another embodiment of the invention, employing a two-layered pattern-support member of the present invention.

In this regard, in the present invention, such types of material are fabricated to provide a one-layered embodiment of the pattern 14, as illustrated, generally by example, in FIG. 19; and to provide a two-layered (or multi-layered) embodiment of the pattern 14, as illustrated in FIG. 20. As set forth in FIG. 20, the pattern 14 permits additional, preferred elastic 'stretchability' to facilitate access and positioning (for selected treatment) of the invention's magnetic components, as explained later herein.

The mask assembly 10 is further provided with a plurality or number of magnet components 20, each of which is provided with a "+" or positive pole or charge (North Pole) and a "−" or negative pole or charge (South Pole), as illustrated in several examples in FIGS. 6A, 6B, 6C, 6D, 6E, 6F and 6G. As will be explained, herein, and as understood generally within the theory of magnetism, when respective magnets of the magnet components 20; each, themselves having positive and negative domains or portions; are properly so positioned, as illustrated by example, they have a magnetic differential between themselves to attract and repel in relation to one another, by virtue of their respective adjoining pole or charge pairings.

The mask 10 is also provided with at least one pocket subassembly 22 which is attached to the support pattern 14 in close or proximal proximity to the pivot hole 16. The pocket subassembly 22 is provided with pocketed means 24 for mounting, removing and positioning (when mounted and installed) each of the magnet components 20 in relation to one another for engaging pairings of the magnet components 20, to produce attraction and repulsion between them.

Accordingly, in this regard, each of the magnet components 20 is mounted in the pocket assembly 22, and positioned to engage the magnetic differential by respective pairings of respective magnet components 20, to attract and repel. The magnetic differential, in fact being defined by pairings of respective magnet components 20 where one part of one magnet juxtaposes a part of a second magnet so as to present charges in relation to one another as positive-positive, negative-negative or positive-negative pairings. By so doing, this correspondingly transmits a resulting pulling or pushing force which travels through the support pattern 14 to skin and tissue areas underlying the position at which the mask 10 is installed.

Figure 6A:
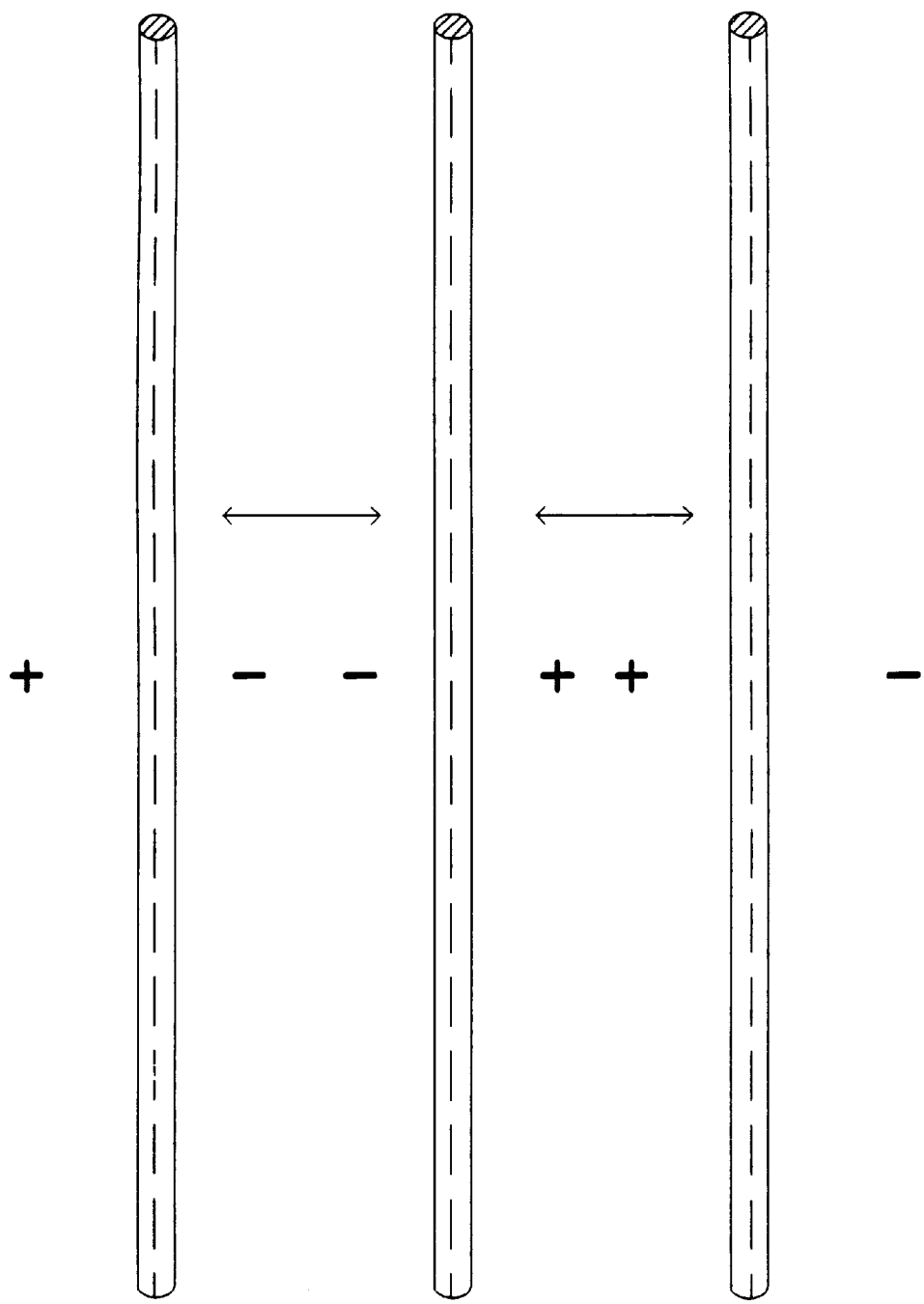
FIG. 6A is a front view illustrating by general example, a group of respective magnet components of the invention, illustrating a magnetic differential by virtue of widthwise positional orientation, where the respective magnet members are placed in a position to repel one another.
Figure 6B:
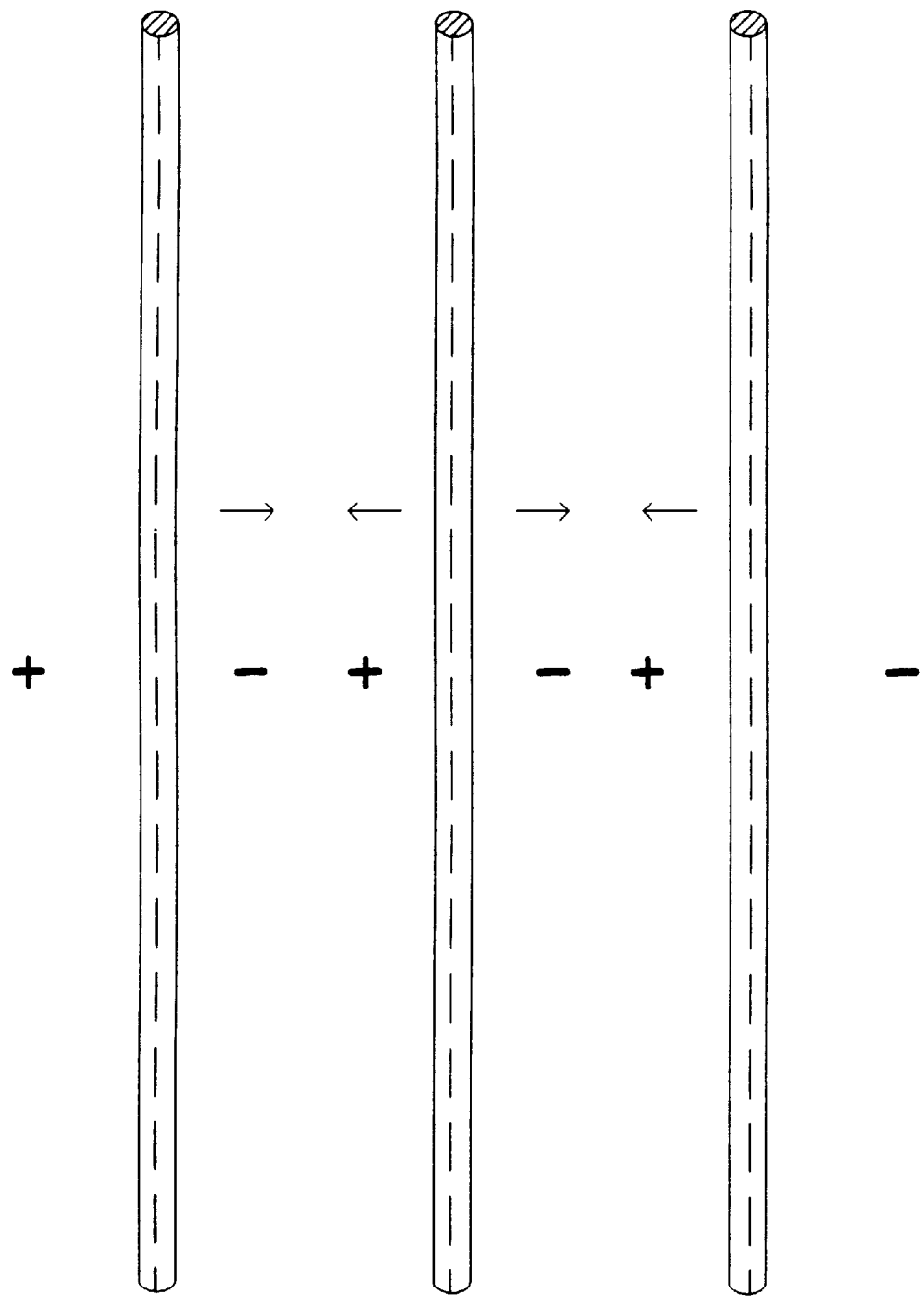
FIG. 6B is a front view similar to that of FIG. 6A, illustrating, by example, a group of respective magnet components of the invention, showing a magnetic differential by virtue of widthwise positional orientation, where the respective magnet members are placed in a position to attract one another.
Figures 6C, 6D:
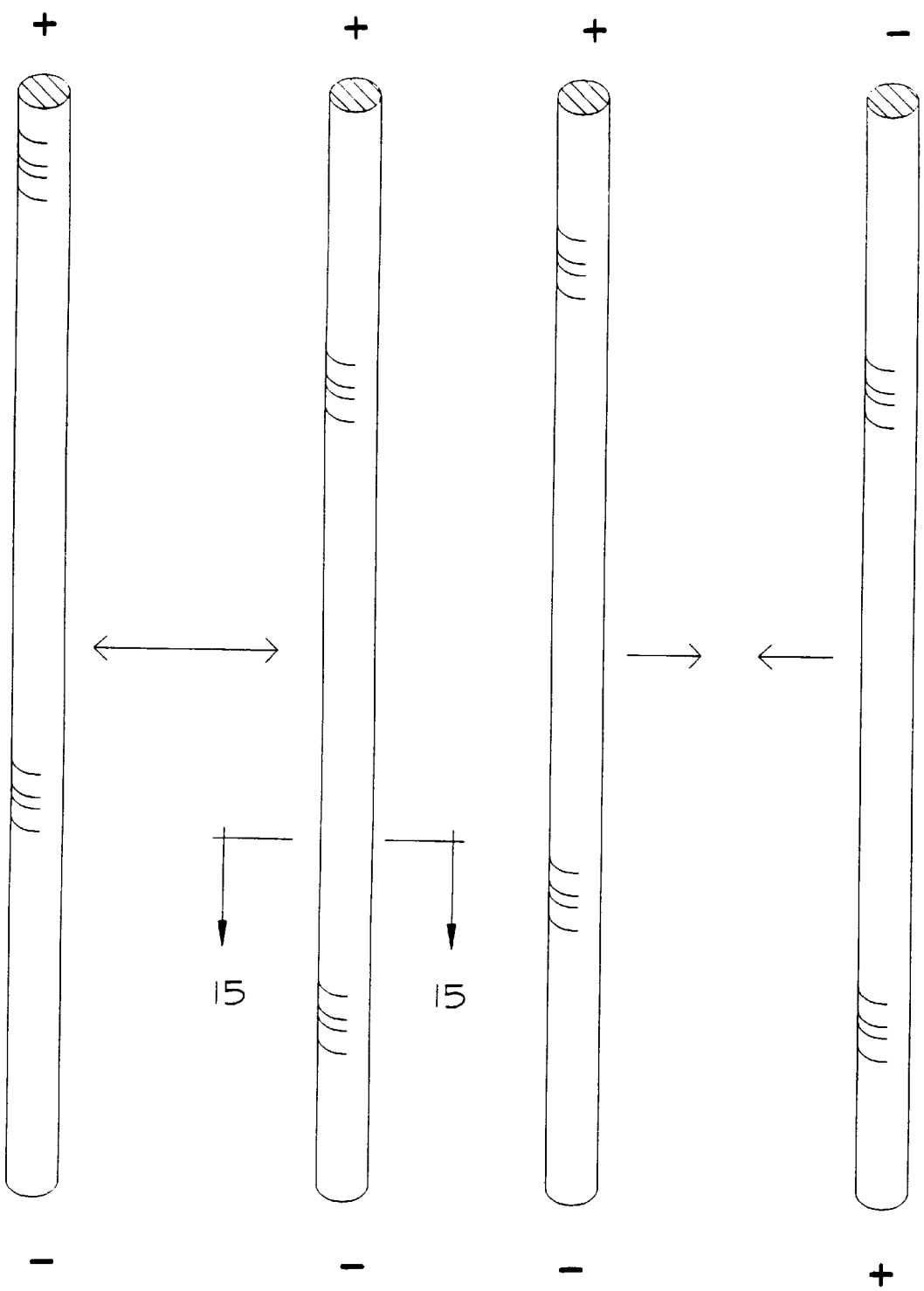
FIG. 6C is a front perspective, illustrating, by example, a group of respective magnet components of the invention, showing a magnetic differential by virtue of lengthwise positional orientation, where the respective magnet members are placed in a position to repel one another.
FIG. 6D is a front view similar to that of FIG. 6C, illustrating, by example, a group of respective magnet components of the invention, showing a magnetic differential by virtue of lengthwise positional orientation, where the respective magnet members are placed in a position to attract one another.
Figure 6G:
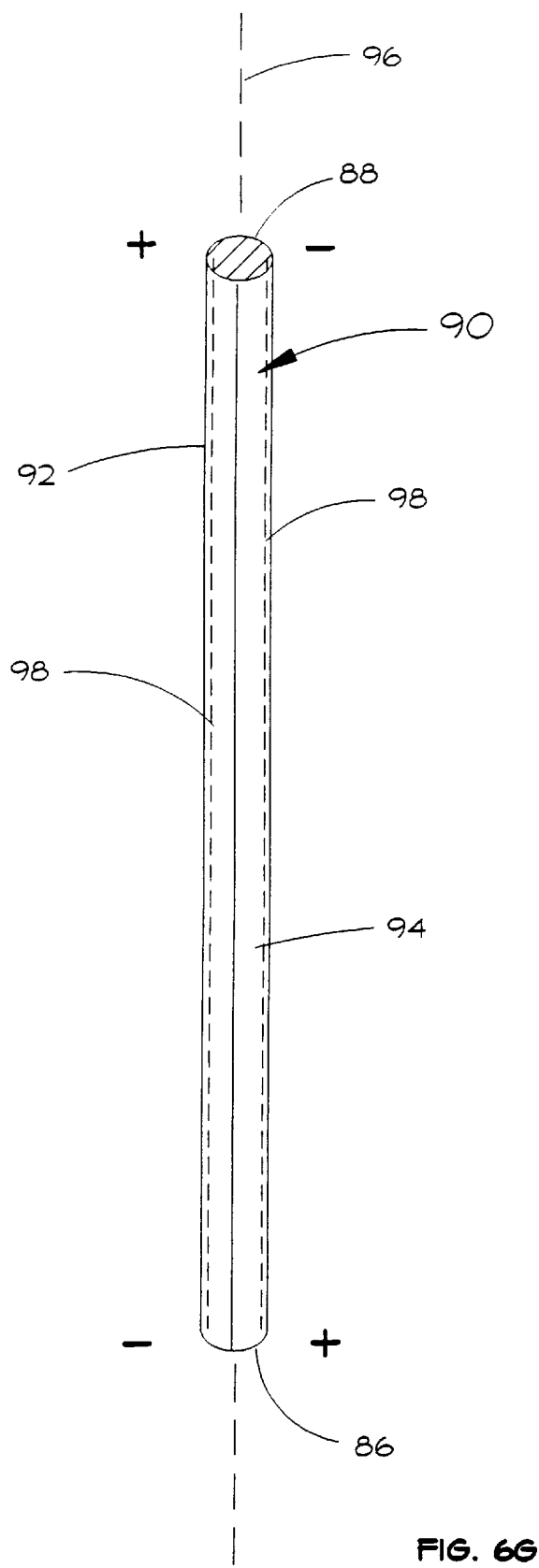
FIG. 6G is a enlarged scale front perspective of a magnet component of the invention, where magnetic differential is set up by widthwise positional orientation of different magnetic poles.
Figure 7:
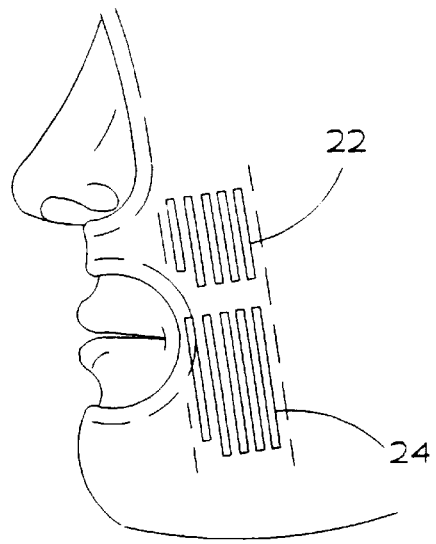
FIG. 7 is a partial side perspective of another embodiment of the invention, showing in general detail part of the face of a treatment recipient with which the invention interacts.
Figure 9:
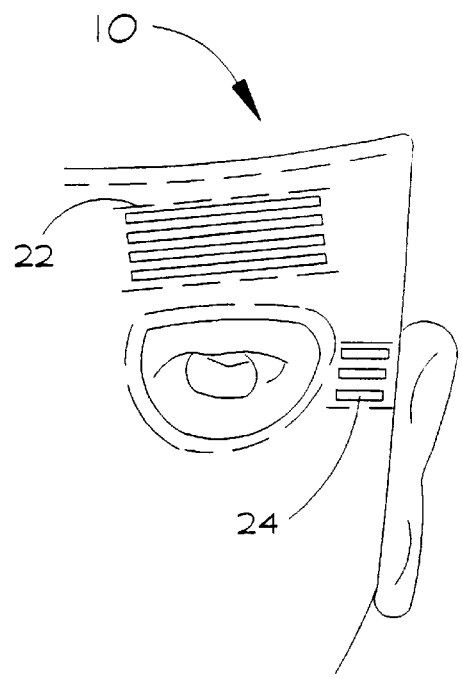
FIG. 9 is a partial front perspective of an embodiment of the invention, showing in general detail part of the face of a treatment recipient with which the invention interacts.
Figure 8:
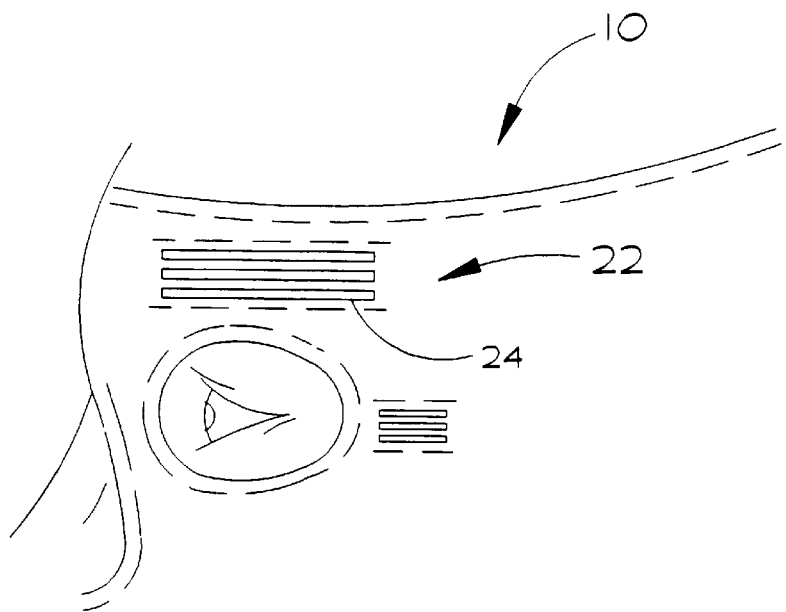
FIG. 8 is a partial side perspective view of an embodiment of the invention.

In included embodiments of the invention each of the magnet components 20 is provided having positive and negative poles adjoining one another by virtue of their opposing positional orientation along a lengthwise axis of the magnet, as shown, by example, in FIGS. 6C, 6D and 6E; and by virtue of their opposing positional orientation along a widthwise axis, as shown, by example, in FIGS. 6A, 6B and 6G.

In one preferred embodiment of the invention the elastic support pattern 14 is provided with the first elastic pivot hole 26, which is designed to be positioned to align generally with a nose area of a treatment recipient or subject when the pattern 14 is secured in an installed treatment position, as illustrated by example in FIGS. 1, 2, 7 and 8. The pivot hole 26 is provided with first lateral 26A, second lateral 26B, anterior 26C and posterior 26D portions, as illustrated in FIG. 3.

Figure 2:
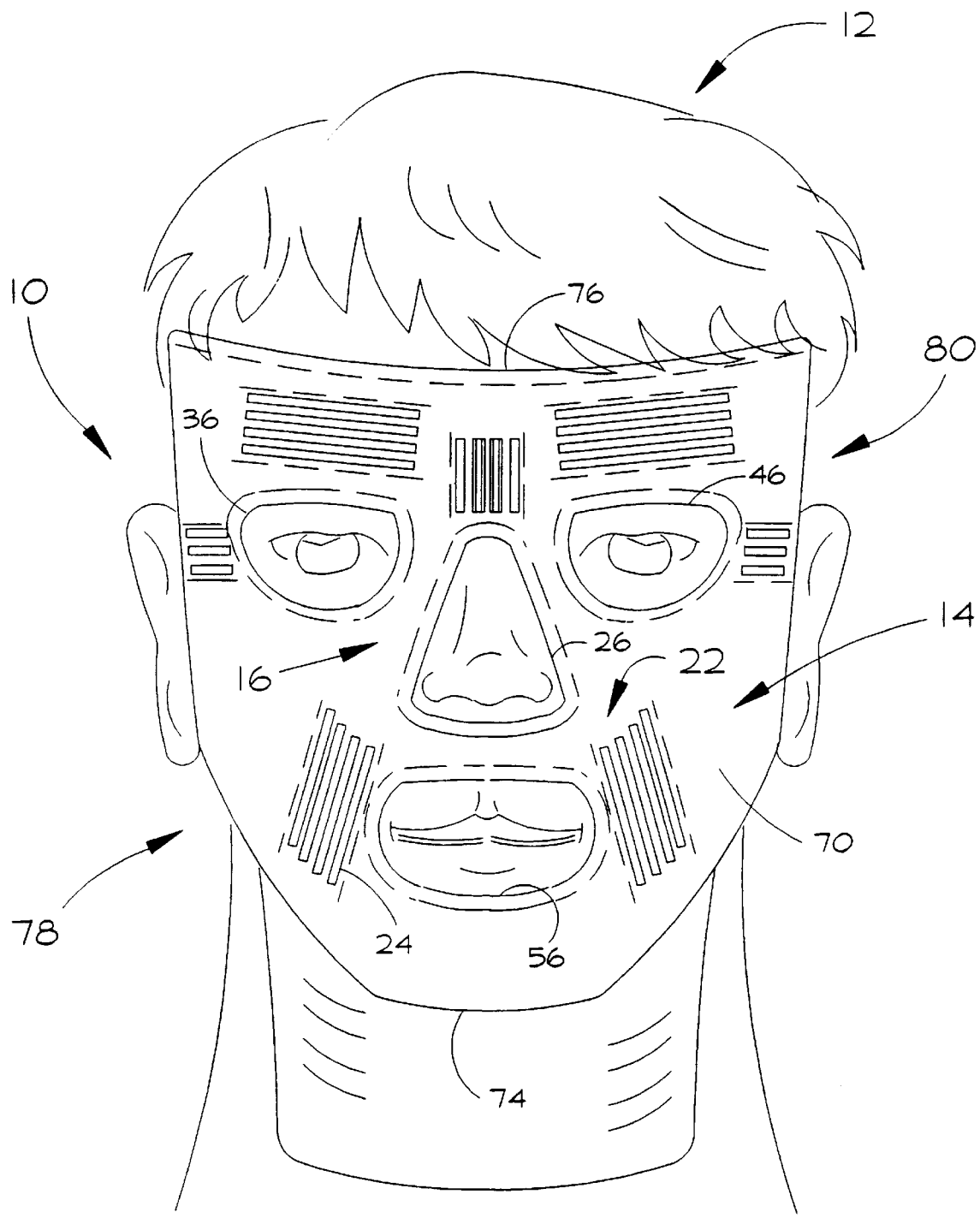
FIG. 2 is a front perspective view of the improved cosmetic and therapeutic mask assembly, and invention, of FIG. 1.
Figure 3:
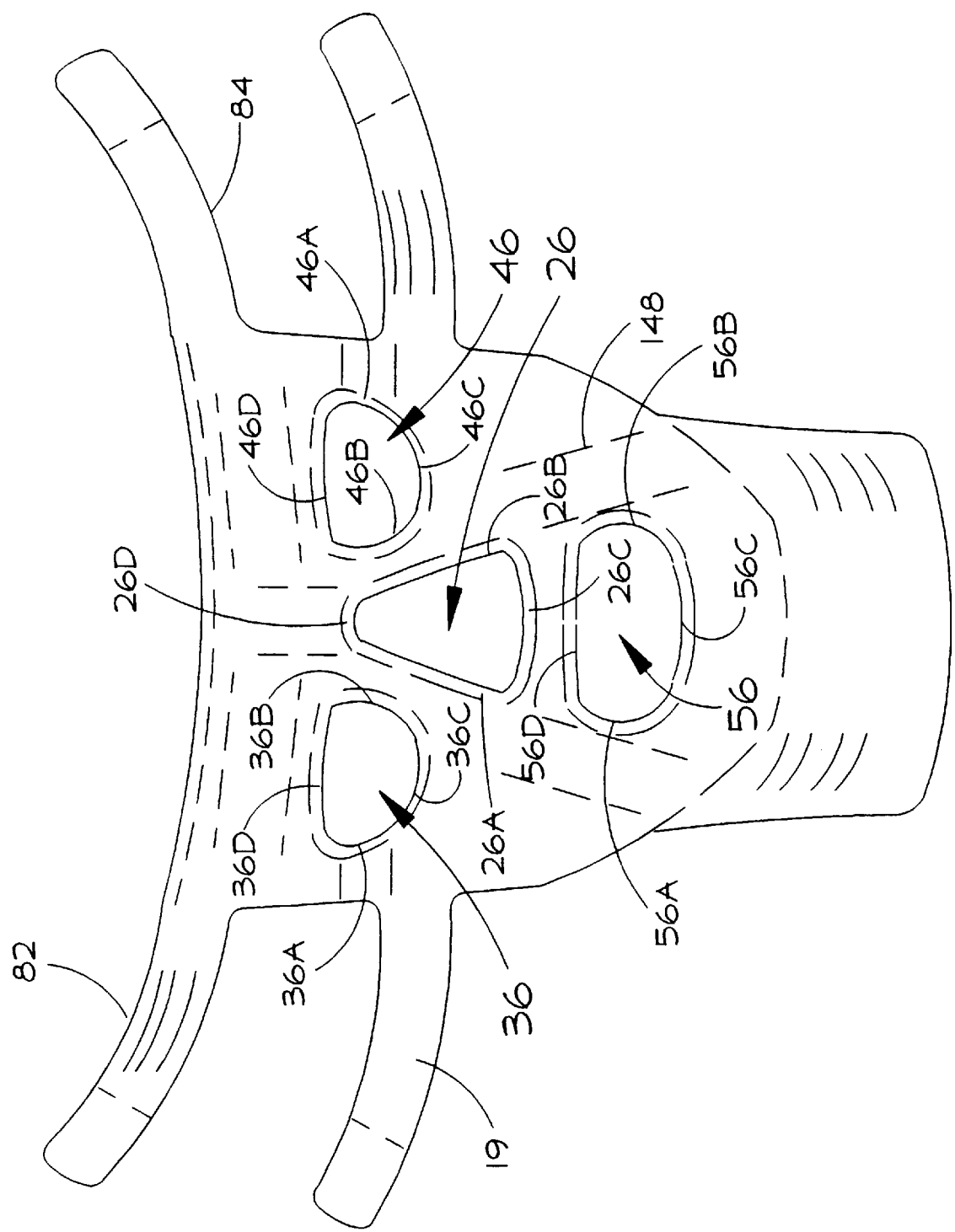
FIG. 3 is a front perspective of a general pattern view of one embodiment of the present inventions with phantom local lines.
Figure 4:
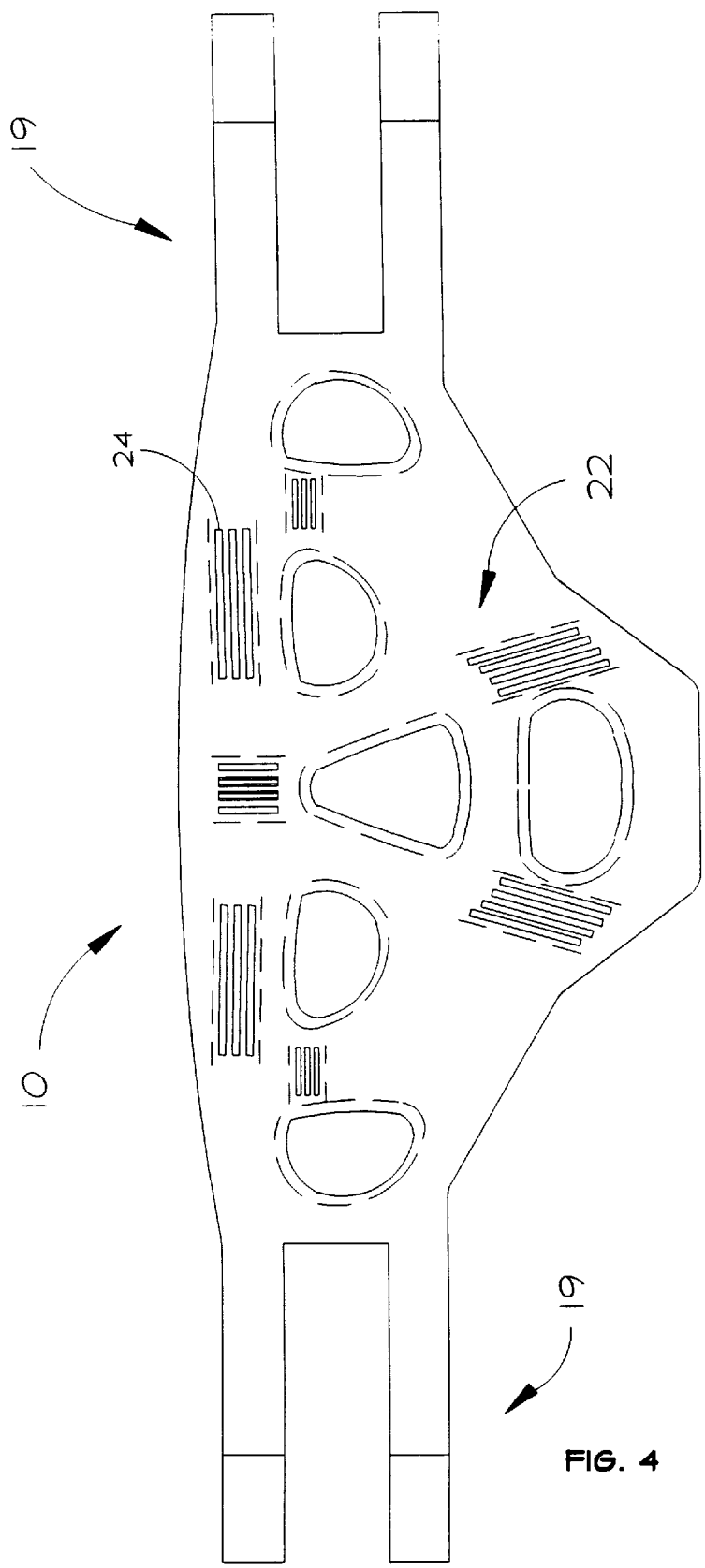
FIG. 4 is a front perspective general pattern view of the embodiment of the invention illustrated in FIGS. 1 and 2.

In this embodiment the pattern 14 is also provided with the second elastic pivot hole 36 and the third pivot hole 46, which are designed to be positioned to align with two eye areas of the treatment recipient as shown in FIG. 2. The second pivot hole 36 is provided with lateral 36A, medial 36B, anterior 36C and posterior 36D portions; and the third pivot hole 46 is provided with lateral 46A, medial 46B, anterior 46C and posterior 46D portions; as shown in FIG. 3.

Additionally, in this embodiment, the pattern 14 also has and defines a fourth elastic pivot hole 56 which is designed to be positioned to align with a mouth or muzzle area of a treatment recipient as shown, by example, in FIG. 2. The fourth elastic pivot hole 56 is provided in this embodiment with first lateral 56A, second lateral 56B, anterior 56C and posterior 56D portions, as shown in FIG. 3.

In preferred embodiments of the invention, the mask 10 is provided with a plurality or number of such pocket subassembly 22, as illustrated by example in FIGS. 1, 2, 4, 7, 8, 9, 12, 13, 14, 16, and 21. As illustrated, each is attached to the support pattern 14 in adjacent or proximal positional relation and proximity to one of the elastic pivot holes 26, 36, 46 and/or 56.

Figure 15:
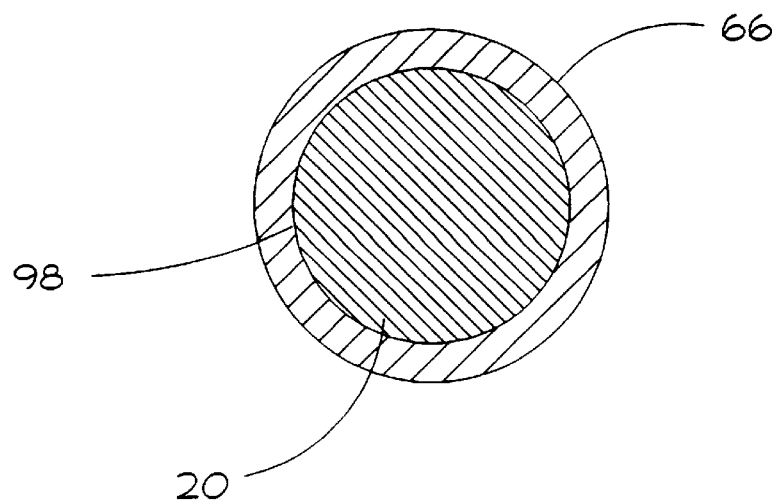
FIG. 15 is a cross-sectional view of FIG. 6C, taken along line 15—15, thereof.

In preferred embodiments of the invention, shown in FIGS. 1, 2, 4, 7, 8, 9, 13, 14 and 15; the pocket means 24 takes the form, within the invention, of a preferably cylindrical or square-like, collar member 66, shown by example in FIG. 15, which houses and supports each of the plurality of magnet components 20; and is, itself, attached to the support pattern 14. In this embodiment, each of the magnet components 20 is installed in a pre-selected position so as to present to adjoining respective components 20 one, or more, of the magnetic differential 'pairings' discussed earlier herein. By further positionings of the magnet components 20, within respective attached collars 66, each of these pairings can be changed to provide respective attraction (pulling) and repulsion (pushing) between respective, various, components 20. Additionally, multi-sectioned and/or jointed magnets 20.5, shown by example in FIGS. 6E and 6F, can be provided to each of the collar members 66 to produce a desired magnetic effect and magnetic differential between adjoining respective, magnet components 20, to treat a selected area of a treatment recipient or area adjacent to each pivot hole 16.

Figure 5:
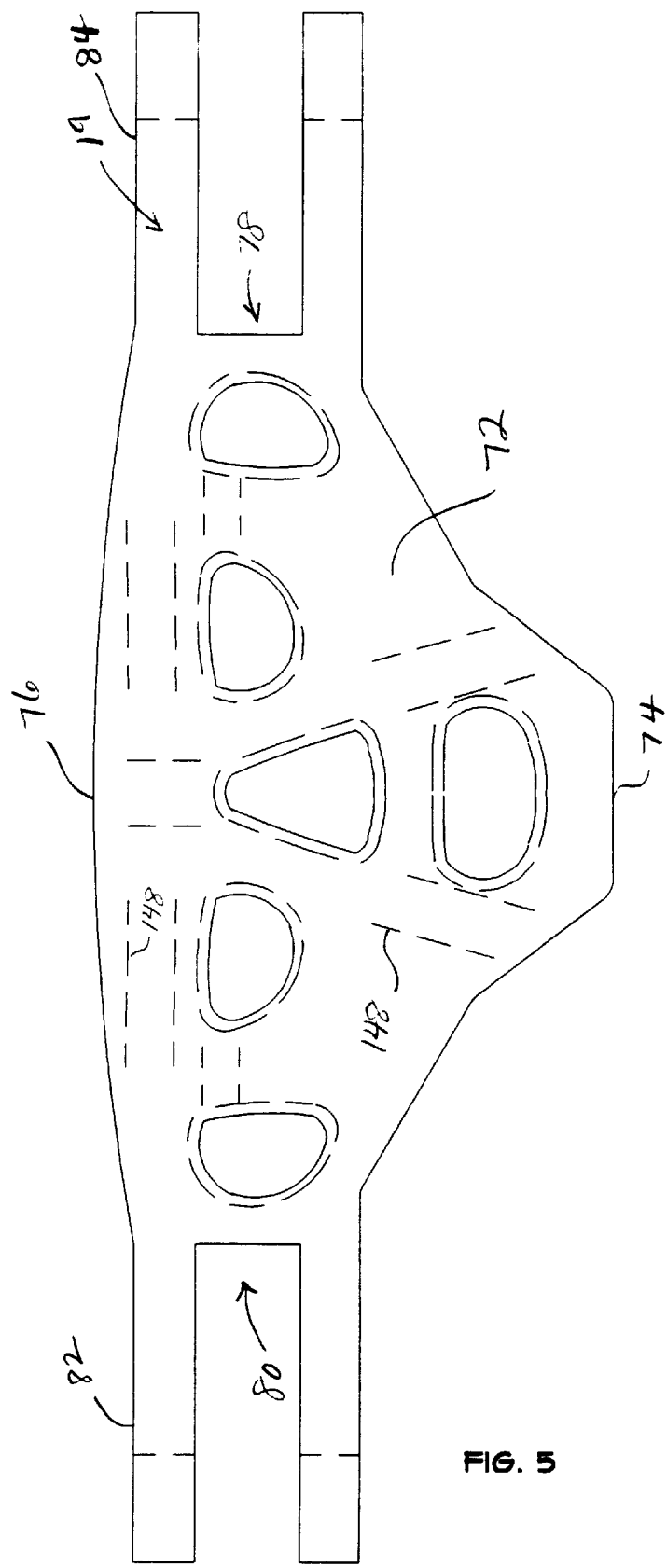
FIG. 5 is a back or opposite side perspective view of the embodiment of FIG. 4, showing in broken lines the stitching securing magnet elements utilized in the invention.

Also, in this embodiment, the pattern 14 is formed by at least one elastic fabriced layer, having first and second surfaces 70 and 72, first and second end portions 74 and 76, and first and second side sections 78 and 80, as shown by example in FIGS. 2 and 5, and other drawings herein.

In preferred embodiments of the invention the strap means 19 is provided with at least a first belt member 82 and a second belt member 84, as illustrated by example in FIGS. 1, 3, 4 and 5. The belt 82 is attached to the pattern 14, in any of a number of diverse fixed or functionally detachable or fixed releasable ways, adjacent or proximate to the second end portion 76 and the first side section 78; and the belt 84 is attached adjacent or proximate to the second end portion 76 and the second side section 80, as illustrated by example in the drawings. It will be understood that the belts 82 and 84 can be attached in other positions in relation to the pattern 14, can be integral in construction, and otherwise provided for securing purposes, or securing the pattern 14 and mask 10, of which it is a part, in many appropriate forms and ways. Also, in additional related embodiments, the strap means 19 is provided with two sets of straps, as illustrated in various drawings herein.

In preferred embodiments of the invention the mask assembly 10 takes the form of a therapeutic assembly for masked positional orientation and magnetic treatment, in interaction with areas of a head of a human treatment recipient. In these embodiments; the first, second, third and fourth elastic pivot holes; 26, 36, 46 and 56; respectively; are designed and positioned to fit in general accordance with the nose, first eye, second eye and mouth areas, respectively, of a human treatment subject.

In these related preferred embodiments of the invention each of the magnet components 20 is a flexible and resilient, cylindrically-configured magnet, as shown by example in FIG. 6G, having first and second ends 86 and 88, a circumferential surface 90 between ends 86 and 88, a first cross-sectional portion 92 and a second cross-sectional portion 94. The portions 92 and 94, as illustrated by example in FIG. 6G, are positioned along a lengthwise axis 96 running, or extending, between the first and second ends 86 and 88. Accordingly, the first cross-sectional portion 92 makes up or generally comprises, part of the radial cross-sectional diameter of each of the magnet components 20; and the second cross-sectional portion 94 makes up or generally comprises another part of the radial cross-sectional diameter of each of the magnet components 20. In this embodiment, the first portion 92 has and defines as a part of its magnetic nature a positive pole or charge and the second portion 94 has and defines as a part of its magnetic nature or makeup a negative pole or charge, as illustrated by example in FIG. 6G and other drawings.

Additionally, in these related preferred embodiments of the invention the collar member 66 is provided in a substantially, cylindrical configuration; and has and defines internally, there within, a collar lumen 98 along its length, as shown generally by example in FIGS. 6G, 19 and 20. In this embodiment each of the magnet components 20 is slid and firmly held in installed position within the lumen 98; and, likewise, is also retrievable or withdrawable, if so desired, from the lumen 98; although it will be understood in this regard that each of the magnet components 20 can be fabricated or constructed already fixed and installed within the lumen 98 of the collar 66, for use as a part of the present invention.

Figure 10:
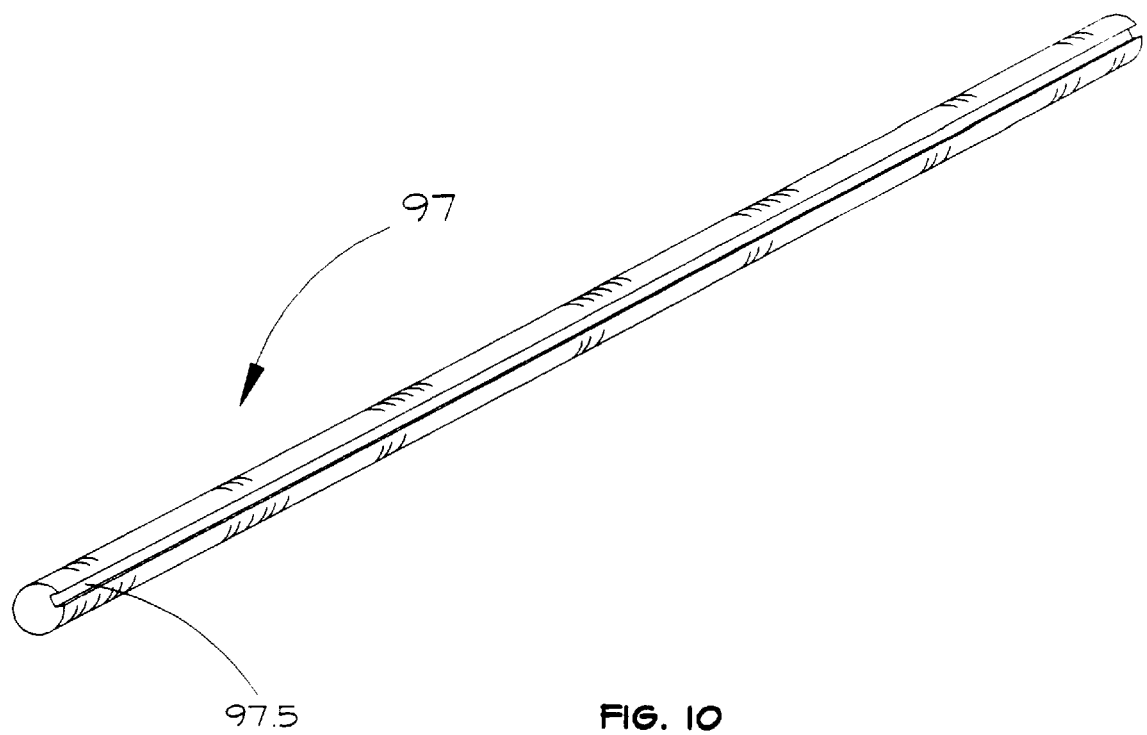
FIG. 10 is an elevated side perspective of one of the respective magnet components of the invention, illustrating the circumferential pivotal notch of one embodiment of the invention.
Figure 11:
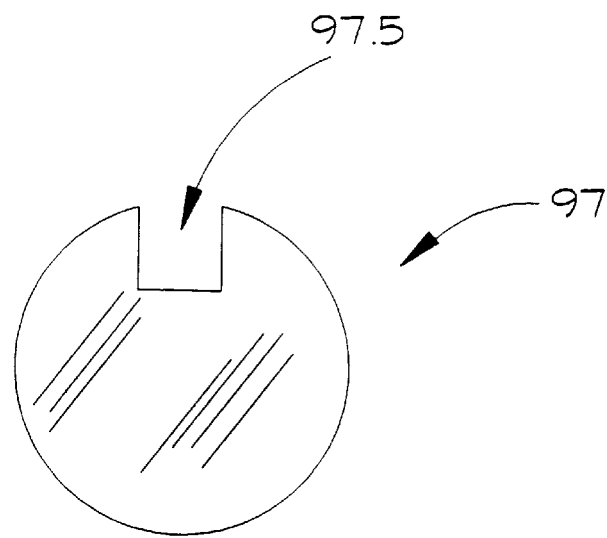
FIG. 11 is an enlarged end view of the magnet component of FIG. 10.
Figure 12:
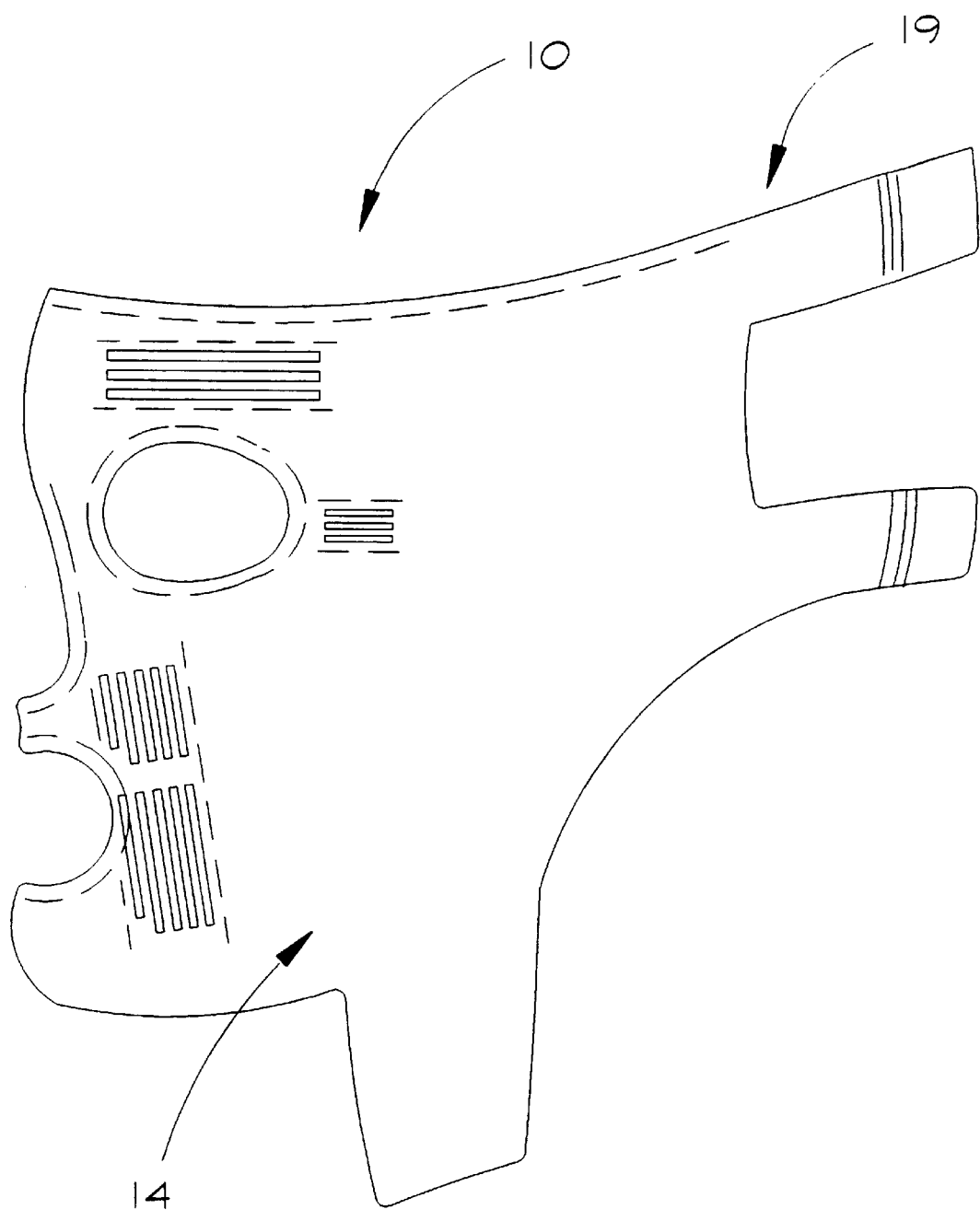
FIG. 12 is a side perspective general plan view of the mask pattern and attached magnet components of one embodiment of the invention.
Figure 13:
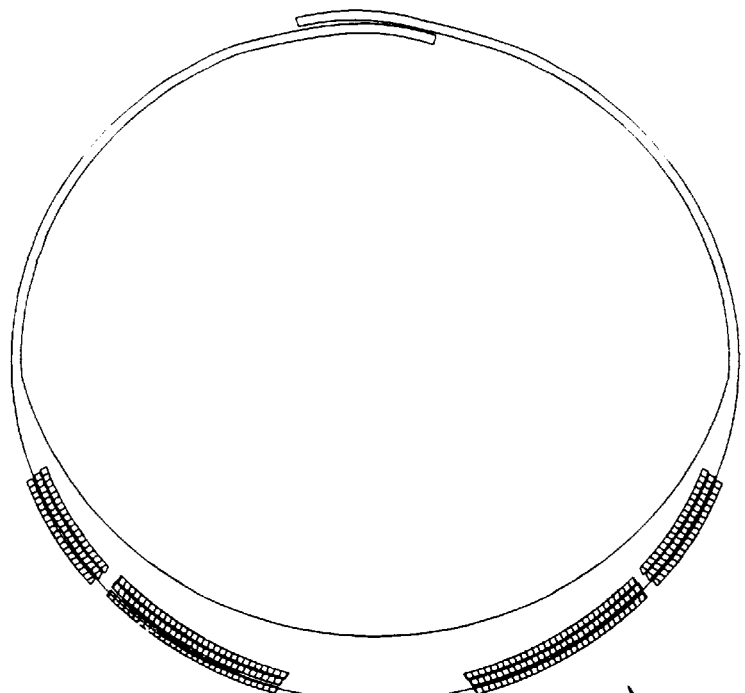
FIG. 13 is an elevated top perspective of one embodiment of the invention.
Figure 14:
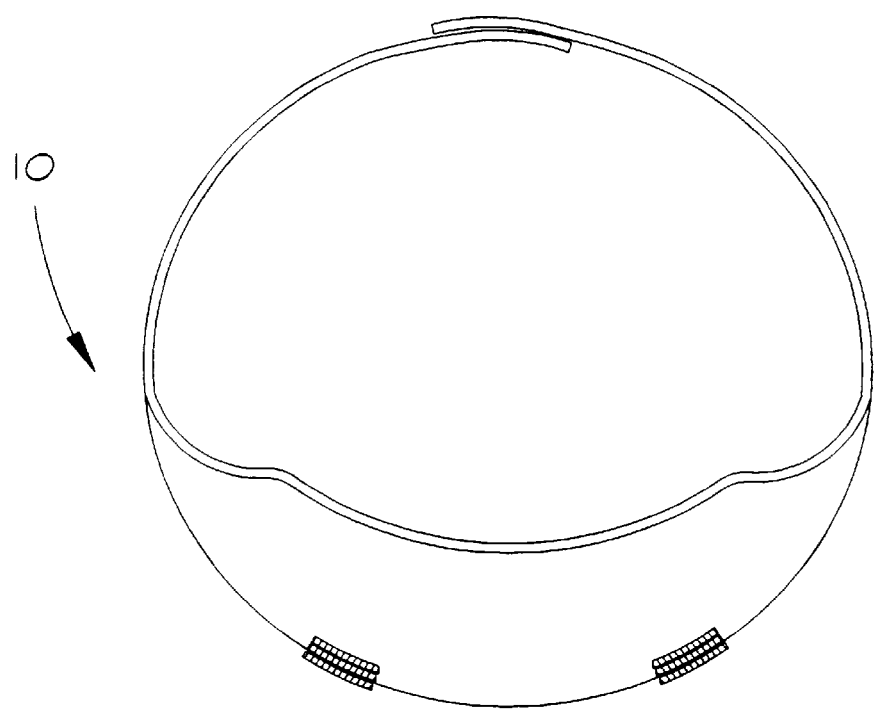
FIG. 14 is a bottom perspective view of the embodiment of FIG. 13.

Also, in this regard, it is within the scope and spirit of the invention to utilize, or utilize selectively or respectively, each of the magnet components 20, without the collar 66, or other envelope-like lining, or other type of specific covering, or covering-like means; in this regard, employing a notched, channeled or grooved magnet member 97 having and defining a positioning groove 97.5 along its surface; lengthwise, widthwise, or otherwise positionally oriented; to facilitate access to and movement or pivoting of the magnet 97; as illustrated, generally by example, in FIGS. 10 and 11. Additionally, it will be understood that other means of facilitating such movement, as a part of respective magnet components 20, themselves, can be utilized within the scope and spirit of the invention, whether designed as a part of the magnet such as the groove 97.5, or attached or adhered thereto.

In this embodiment, the mask assembly 10 is provided with pocketed series assembly means 100 for pivotally positioning each of the magnet components 20 in relation to one another, for selectively engaging the magnetic differential thereof to attract and repel in relation, respectively, to one another; as illustrated by examples in FIGS. 16, 17, 18, 19, 20 and 21.

The assembly means 100 is provided with first, second, third, fourth, fifth, sixth, seventh and eighth elastic biasing pocket subassemblies; 102, 104, 106, 108, 110, 112, 114 and 116, respectively. Each of the just listed elastic-biasing pocket subassembly is provided with two (2) or more fluted pivot pockets 118, in preferred embodiments.

The fluted pivot pockets each have and define an installation channel 120 and at least one installation opening 122 communicating or linking up with the channel 120; and each is further provided in preferred embodiments with at least one rounded access groove 124 which communicates or extends through lateral or lengthwise portions of the the pocket to link the outside with the installation channel 120; as illustrated in FIGS. 16, 19, 20, 21 and other drawings herein.

The fluted pivot pockets 118 of each of the subassemblies 102, 104, 106, 108, 110, 112, 114 and 116 are preferably attached to the support pattern 14 (stitchedly, fixedly and/or detachably) so as to be positioned lengthwise in series and in adjacent juxtaposition with one another, as illustrated; though it will be understood that is within the scope of the invention to place them in other positional or configurational orientation, adjacently and magnetically proximate, in relation to one another.

In this preferred embodiment the first elastic-biasing pocket subassembly 102 is attached to the support pattern 14 in close or adjacent positional proximity to the first lateral portion 26A of the first elastic pivot hole 26. The second pocket subassembly 104 is attached close or adjacent to the lateral portion 36A of the second pivot hole 36; and, accordingly, in like manner, the third pocket subassembly 106 close to the posterior portion 36D (or superior area, anatomically, of the eye); the fourth subassembly 108 close to the first lateral portion 56A of the fourth pivot hole 56; the fifth subassembly 110 close to the second lateral portion 26B of the first pivot hole 26; the sixth subassembly 112 close to the lateral portion 46A of the third pivot hole 46; the seventh subassembly 114 close to the posterior portion 46D (or superior portion, anatomically, of the second human eye) of the third pivot hole 46; and the eighth elastic-biasing pocket subassembly 116 in close or adjacent positional proximity to the second lateral portion 56B of the fourth elastic pivot hole 56; as illustrated, generally by example, in FIGS. 16, 21, 24, 25, 26, 27 and 28 of the drawings.

In this embodiment, each of the magnet components 20 is mounted in a respective fluted pivot pocket 118, of the respective pocket subassemblies 102, 104, 106, 108, 110, 112, 114 and 116; and when so mounted, each of the magnets 20 is selectively accessible and positionable (movable or pivotable) by virtue of manual or other access through each of the respective rounded access grooves 124. and by do doing, the magnetic differential previously discussed can be engaged, by respective magnet component 20 'pairings,' to produce attraction and repulsion between such pairings of positioned magnet components 20; therefore, conducting, transmitting or communicating this magnetic differential (or cumulative magnetic charge), and resulting "pulling" and "pushing" respective forces, through (and/or through and with) the elastic support pattern 14 to bring these forces (and physical movement/massage and therapeutic benefit) to bear at or on adjacent areas of the human head of a treatment recipient with which the support pattern 14 adjoins, lies against and interacts. The same type of benefits and structural elements and use of the present invention is of benefit in adapted embodiments for use in interaction with small and large animals.

It will be appreciated, as stated earlier in regard to the objects of the present invention, and within the scope and spirit thereof; that each of the preferred embodiments of the present invention is designed to support the magnet components 20 in very close (and/or generally flush, proximal or proximate) positional relation to the skin or outlying tissue of a human or animal subject; and to efficiently minimize the loss of magnetic, or magnetic or poled differential, power between adjacent magnetic components 20, as a function of the distance from treatment area 'squared' ($D^2$) (or magnetic power loss [$MPL$]=$D^2$).

In preferred embodiments, each of the fluted pivot pockets 118 is constructed or fabricated from gros grain ribbon-polyester material or other banded and/or biasing or elastic fabric or material; each, of the nature, by virtue of its physical or chemical makeup, so that it will not substantially impede or limit magnetic charges, field and/or differential. The balance of the assembly means adjoining and or supporting the respective fluted pivot pocket 118, is, similarly, fabricated from a 'magnetic-friendly' and stretchable or elastic material which c;an be chosen from a diverse number of cotton, polyester, wool, alloy materials, and other compatible substances. It will be understood, within the scope of the invention, that the pockets 118 can be fabricated individually or integrally in positional relation adjoining one another as a part of a respective assembly means 100; and can, by virtue of this, or by such a positional orientation, substantially or totally comprise the means 100; and/or that different constructive materials, as set forth, can be utilized in part to makeup the pockets 118 and adjoining supporting portions of the means 100, when utilized.

In preferred related embodiments, the magnetic components 20 are chosen from some several types of cylindrical, rod, or linear square-like, magnetically and physically resilient, flexible magnets such as, for example, the "Sintered Alnico 5" magnet material manufactured by Adams Magnetic Products Company, 7061 Grand National Drive, Suite 117, Orlando, Fla. 32819 (and having additional midwest, southwest, northeast and west divisional offices and locations), and also ceramic magnetic material and some several of their diverse line of magnetic products; and magnetic material manufactured by Bunting Magnetics Company, 500 S. Spencer Avenue, Box 468, Newton, Kans. 67114 (and other locations).

Additionally, in this regard, a number of diverse types of small magnets with low 'gauss' values, manufactured by a number of concerns, can be effective and functional, as the magnetic components 20 of the present invention; in that body tissue is found, and reported in the literature, to be very susceptible and transparent, if you will, to magnetic fields. In this regard, magnetic penetration can be from 5 to 20 cm., depending on the magnetic field strength employed. Also, it is submitted that part of the benefits of the magnetic differential, and magnetic field, brought to bare upon areas of a treatment recipient by the mask 10 can improve circulation, control pH balance, and augment in the anatomy and physiology of the skin and subcutaneous and adjacent areas a more healthy physical condition and appearance when used by, or employed upon, a treatment subject for a little as 10 (ten) to 15 (fifteen) minutes, or so, on a daily basis.

Additionally, a number of types of magnets can be utilized as the magnetic components 20 to bring about the magnetic differential and magnetic 'pairings' previously discussed as being utilized in the present invention.

In this regard, magnetic materials can be employed where the direction of magnetism (or divergent magnetic poles or charges) of the magnet component 20 is: (1) parallel to its length; (2) parallel to its thickness; (3) consecutively, multiply poled adjacently in series; (4) two or multi-poled on one of its faces or surfaces; (5) parallel to its length; (6) parallel to its thickness or width; (7) radially oriented in series, alternatively or cross-sectionally; (8) four or multi-poled on one or more of its same axial faces or surfaces; and/or (9) bi-polar on one of its same faces or surfaces.

It will also be appreciated within the scope and spirit of the invention, and as set forth earlier in relation to the objects of the invention; that the fabric or constructive material of one or more layers of the support pattern 14 is also selected in keeping with the need addressed by the present invention in being able to utilize lotions, creams, or other health, beauty or therapeutic fluids, in combination with the invention, and on the skin or overlying tissue of a treatment recipient, which the pattern 14 covers when in installed position, when such fluid is utilized, and with which it therapeutically cooperates and enhances when so employed.

Therefore, such constructive material is also selected with the inherent ability to be laundered, washed or cleaned, after such fluids have been utilized, when this is the case, in cooperation or combination therewith.

Also, the layering of the support pattern 14 is illustrated, by example, in FIG. 19 as single-layered in nature; and in FIG. 20 as double or dual-layered (multi-layered) in nature. In preferred embodiments of the present invention, the two-layered, pattern 14 facilitates the ability of the pattern 14 to extend flexibility and movement of respective fluted pivot pockets 118 when respective magnet components 20 are installed therein; acting in a base-elastic support function to permit sliding and extension of respective pocketed magnets and their extension over adjacent skin and tissue areas of a treatment subject. When utilized, as preferred, in this manner, the second layer 126 of the pattern is substantially a mirror-image fit (configurationally and structurally) with the first layer 128 of such an embodiment of the present invention; and the two layers 126 and 128 are so attached or fixed, stitchedly or otherwise, with one another; so that the second layer 126 is inboard of the first layer 128, and utilized in making flush contact and fitting with the skin and tissue of a treatment subject. The strap means 19 is accordingly adapted to fit in connection with both such layers 126 and 128; and to hold both layers snugly onto the treatment subject.

The constructive material utilized in the fabrication of each of the layers 126 and 128 is as discussed above with regard to the constructive materials of the support pattern 14.

Figure 21:
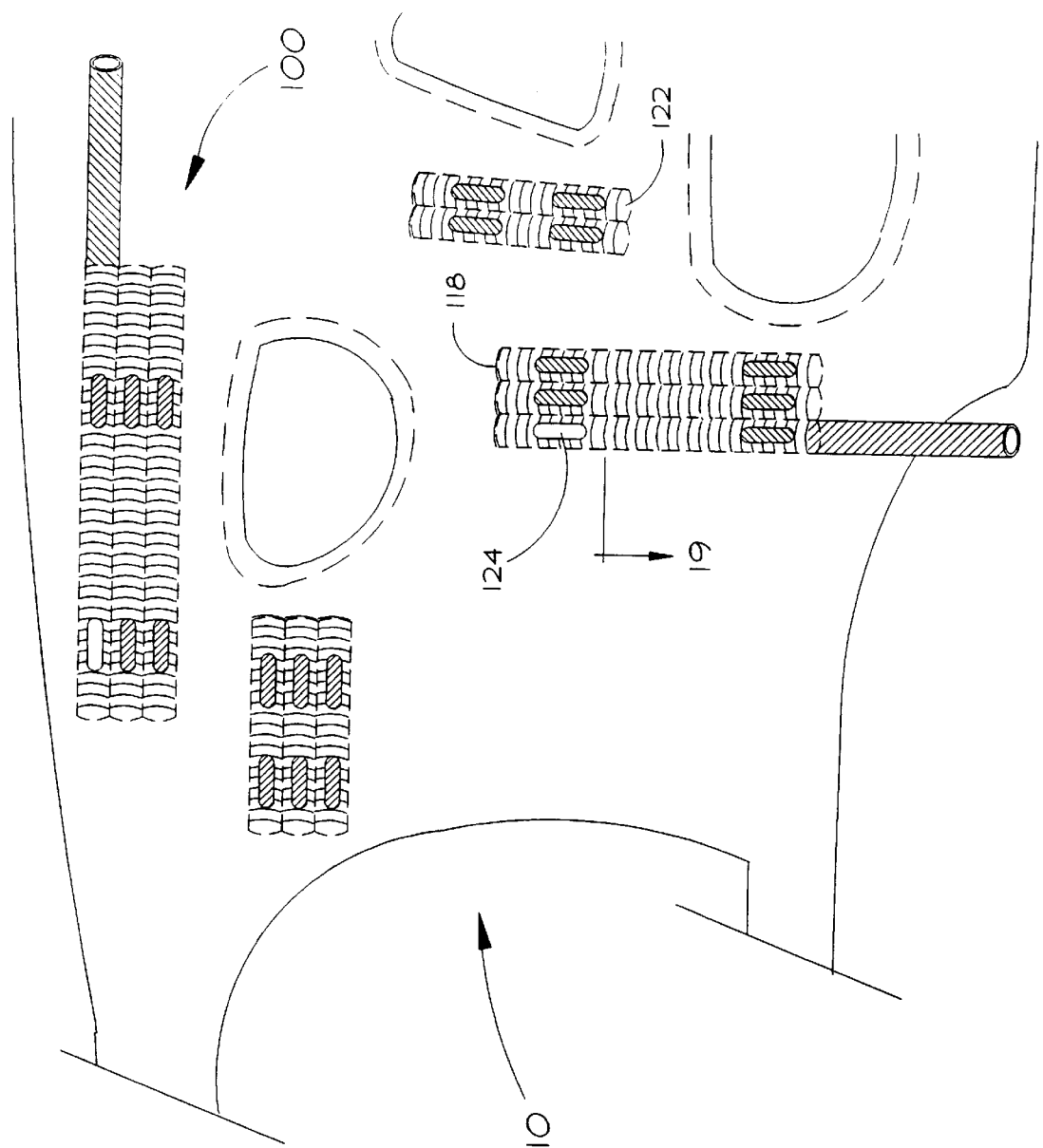
FIG. 21 is a similar view to that of FIG. 16, illustrating the selective retrievable nature of magnet components installed in this embodiment.

As illustrated in FIG. 21, and in keeping with the objects of the present invention, each of the magnet components 20 are preferably retrievable and replaceable in relation, and with regard, to each of the fluted pivot pockets 118 or pocket subassembly 22 of the present invention.

In additional preferred embodiments of the invention the elastic pivot hole 16, or the cumulative configurational nature of the pivot holes 26, 36, 46 and 56; which, each, themselves, is stretchable and extendable by virtue of their definition from the flexible constructive material utilized for the pattern 14; is adapted within the scope of the present invention, in integral trapezoidal configurations, such as 150 illustrated, by example, in FIG. 22; and can also be shaped, as so adapted, in a parabolic (or parabola-like) configuration, such as 152 illustrated in FIG. 23.

In each case discussed just above, respective assembly means 100, with their included fluted pivot pockets and installed respective magnet components 20, are installed proximate, proximal (structurally closer to) or adjacent to the perimeter of each configuration of these respective embodiments of the pivot hole 16 (or cumulative previous areas of pivot holes 26, 36, 46 and 56), so that they can be extended, while employing a magnetic differential or field, as earlier set forth, to treat and therapeutically address areas proximal to the sense organs 18, shown in general detail in FIGS. 22 and 23. It will be understood, within the scope of the present invention, that other perimeter shapes and configurations can be effectively utilized to define the pivot holes discussed, with attached positioning of the assembly means 100 on the pattern 14, near the perimeters of such configurations; to address statically and by flexible extension of the pattern 14 selected treatment areas of a head, face or other body area. The configurations discussed herein are, therefore, by example only, without limitation to the full scope and spirit of the invention.

Additionally, in preferred embodiments, the constructive material utilized and comprising the respective fluted pivot pockets 118 can be of such a nature so that banded or fabriced biasing forces are employed by the nature of the chosen constructive material, for novel use in the present invention.

Figure 17:
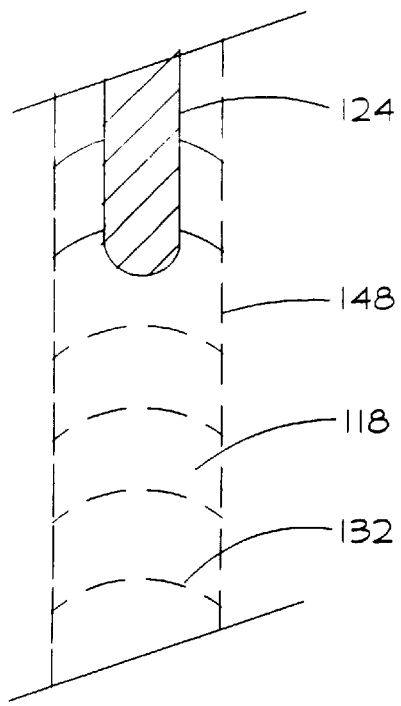
FIG. 17 is a partial top view of one of the respective magnetic components of the invention, illustrating the fluted pocket of the invention and biased, widthwise cross-stitching in broken lines.
Figure 18:
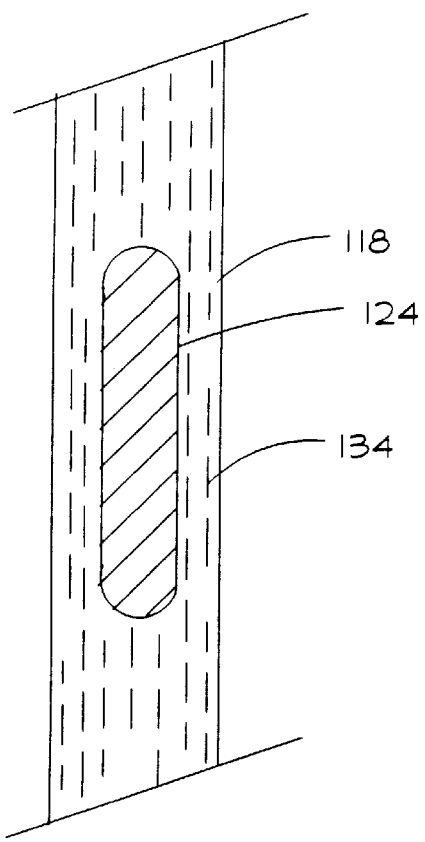
FIG. 18 is a partial top view of one another embodiment of one of the respective magnetic components of the invention, illustrating the fluted pocket and biased, lengthwise cross-stitching in broken lines.

In this regard, examples of such biasing forces brought to bare by these preferred types of materials are illustrated by example with respect to cross-radial biasing fabriced elements 132 in FIG. 17; and lengthwise biasing fabriced elements 134; in relation to the pocket's 118 construction, in FIG. 18.

Similar and other such materials, so utilized in the present invention, elastically or biasingly bring about various directed forces, thereby holding the respective magnet components 20 in the respective pockets 118, as utilized.

With respect to the multi-sectioned or jointed magnet 20.5, illustrated by example in FIG. 6F, the magnet joint meniscus element 140 is provided between jointed-magnet subportions 21.5, illustrated by example in FIG. 6F, to facilitate flexibility and bending of subportions 21.5 for more sensitive positioning, in use of the present invention, in accordance with the contours or configuration of selected treatment areas of a treatment subject or recipient.

Additionally, with regard to constructive materials of the collar member 66, when this element is employed in preferred embodiments of the invention; such materials can be chosen from light polymer or plastic material (of straw-like thickness and makeup), fabric, substance or other material or substance which is 'magnetically-friendly' and not burdensome and/or substantially detracting or limiting from the expressed, intended purposes and use in the present invention of magnetic differential and magnetic field, and the novel process inherent in this.

Accordingly, the appended claims are intended to cover all changes, modifications and alternative options and embodiments falling within the true breath, scope and spirit of the present invention. The reader is, therefore, requested to determine the scope of the invention by the appended claims and their legal equivalents, and not by the examples which have been given.

I claim:

1. A therapeutic assembly for masked positional orientation and magnetic treatment, in interaction with a face or head of a treatment recipient, said therapeutic assembly comprising:
    an elastic support pattern, defining at least one elastic pivot hole, positioned to align proximally, when in an installed position for treatment use, with a sensing structure-organ of a face or head, and means for so securing the elastic support pattern in an installed position;
    a plurality of magnet components having, when so positioned, a magnetic differential thereof to attract and repel in relation to one another; and
    at least one pocket subassembly being attached to the elastic support pattern, adjacent positionally to the at least one elastic pivot hole, having means for removably mounting and pivotally positioning each of the plurality of magnet components in relation to one another for selectively engaging the magnetic differential thereof to attract and repel;
    each of said plurality of magnet components being mounted in the at least one pocket subassembly and selectively positioned, when so mounted, to, thereby, engage the magnetic differential thereof to attract and repel, to correspondingly transmit a resulting pulling and pushing force, respectively, through the elastic support pattern to areas of the face or head of a treatment recipient with which the therapeutic assembly interacts.

2. The therapeutic assembly of claim 1, wherein:
    each of the plurality of magnet components comprises a north pole end and a south pole end, spaced from one another along a lengthwise axis.

3. The therapeutic assembly of claim 1, wherein:
    each of the plurality of magnet components comprises a north pole cross-sectional portion and a widthwise-adjoining and juxtaposed south pole cross-sectional portion.

4. The therapeutic assembly of claim 1, wherein:
    said elastic support pattern defines a first elastic pivot hole having first lateral, second lateral, anterior and posterior portions, positioned thereon to align generally with a nose area of a treatment recipient when in an installed position; and second and third elastic pivot holes each having lateral, medial, anterior and posterior portions, positioned thereon to align, respectively, with each of two eye areas of a treatment recipient when in an installed position.

5. The therapeutic assembly of claim 4, wherein:
    said elastic support pattern further defines a fourth elastic pivot hole having first lateral, second lateral, anterior and posterior portions, positioned thereon to align generally with a mouth or muzzle area of a treatment recipient when in an installed position;
    each of said elastic pivot holes being selectively usable to further extend the elastic support pattern, thereby facilitating selected extension and access to, and effect of, the magnetic differential to selected adjacent areas of a treatment recipient.

6. The therapeutic assembly of claim 5, wherein:
    said therapeutic assembly comprises a plurality of pocket subassemblies, each being attached to the elastic support pattern in adjacent and proximal positional relation to one of the elastic pivot holes, and each defining a plurality of fluted pivot pockets, each of the magnet components being retrievably installed, respectively, in each of the fluted pivot pockets; whereby access is selectively obtainable to position and pivot each of the magnet components in relation to one another and in relation to adjacent areas, when the therapeutic assembly is installed, of a treatment recipient.

7. The therapeutic assembly of claim 5, wherein:
    said elastic support pattern has at least a first elastic fabriced layer having first and second surfaces, first and second end portions and first and second widthwise portions, each of said first and second widthwise portions having first, second and third subportions; and
    said means for so securing the elastic support pattern in an installed position comprises at least a first belt member and a second belt member, said first belt member being fixedly attached to the elastic support pattern in adjacent positional relationship to the second end portion and the third subportion of the first widthwise portion, and said second belt member being fixedly attached to the elastic support pattern in adjacent positional relationship to the second end portion and the third subportion of the second widthwise portion.

8. The therapeutic assembly of claim 7, wherein:
    each of the plurality of magnet components comprises a flexible and resilient, cylindrically-configured magnet having first and second ends opposing one another along a lengthwise axis and defining a circumferential surface therebetween, said first end defining magnetically and having a north or positive pole, said second end defining magnetically and having a south or negative pole, and the circumferential surface defining and having a notched position groove for radial or circular pivoting thereof, and
    wherein the at least first elastic fabriced layer comprises a mesh fabric material defining surfacing suitable for transmitting and communicating a magnetic differential therethrough.

9. The therapeutic assembly of claim 7, wherein:
    each of the plurality of magnet components comprises a flexible and resilient, cylindrically-configured magnet having a first cross-sectional portion and a second cross-sectional portion, divided by a lengthwise separation axis positionally oriented therebetween, said first and second cross-sectional portions being fixedly attached in juxtaposition to one another, and further extending in positional orientation along the lengthwise separation axis, the first cross-sectional portion defining, magnetically, and having a north or positive pole, the second cross-sectional portion defining, magnetically, and having a south or negative pole.

10. The therapeutic assembly of claim 9, wherein:
    each of the cylindrically-configured magnets further comprises a cylindrically-configured collar member, said cylindrically-configured collar member defining a lengthwise oriented lumen through and within which each cylindrically-configured magnet is slideably and retrievably installed;

and wherein said means for removably mounting and pivotally positioning each of the plurality of magnet components in relation to one another, comprises a plurality of pocket members, each of the pocket members having a fluted enclosure member having first and second ends opposing each other along a lengthwise axis thereof, first and second widthwise flap portions, and first and second surface portions, the fluted enclosure member defining at least one rounded groove along the lengthwise axis extending between the first and second surface portions, the first and second widthwise flap portions each being stitchedly attached to the elastic support pattern, and, when so attached, thereby defining first and second open ends and a hollow channel therebetween;

whereby a plurality of cylindrically-configured collar members, each with an installed cylindrically-configured magnet member, are slideably installed within the channel, each of the collar members being pivotable and positionable in relation to one another by access through each of the rounded grooves, respectively, of each of the fluted enclosure members of each of the pocket members; and wherein the at least first elastic fabriced layer is constructed of meshed fabric having the ability to transmit and communicate a magnetic differential.

11. The therapeutic assembly of claim 7, wherein:

each of the plurality of magnet components comprises a generally cylindrical magnet of flexible and resilient construction and a flexible magnet collar member, the flexible magnet collar member defining a lumen, the generally cylindrical magnet being slideably inserted within the lumen, thereby being covered by said flexible magnet collar member.

12. The therapeutic assembly of claim 11, wherein:

the generally cylindrical magnet further comprises a plurality of magnetic sub-parts, aligned to establish a magnetic differential between themselves, when so inserted within the flexible magnet collar member, and to establish a magnetic differential between each of the plurality of magnetic components when selectively so positioned.

13. The therapeutic assembly of claim 12, wherein:

the generally cylindrical magnet further comprises a plurality of elastic joint-end members, each of which is positioned in alignment within the lumen between each of said magnetic sub-parts, for bending the magnetic sub-parts in reference to each other and in response to a configurational area of a treatment recipient.

14. The therapeutic assembly of claim 7, wherein:

said therapeutic assembly comprises first, second, third and fourth pocket subassemblies, each of said pocket subassemblies being attached to the first elastic fabriced layer of said elastic support pattern, said means for removably mounting and pivotally positioning each of the plurality of magnet components in relation to one another comprising, within each of said pocket subassemblies, a plurality of fluted pivot pockets each defining at least one rounded entry channel, each of the magnet components being retrievably installed, respectively, in each of the fluted pivot pockets, for selected access through each respective rounded entry channel, to position and pivot each of the magnet components in relation to one another when each of the pocket subassemblies is positioned and installed over a treatment area of a treatment recipient;

the first pocket subassembly being attached to the elastic support pattern in proximal and adjacent positional orientation in relation to the first lateral portion of the first elastic pivot hole;

the second pocket subassembly being attached to the elastic support pattern in proximal and adjacent positional orientation in relation to the lateral portion of the second elastic pivot hole;

the third pocket subassembly being attached to the elastic support pattern in proximal and adjacent positional orientation in relation to the posterior portion of the second elastic pivot hole; and the fourth pocket subassembly being attached to the elastic support pattern in proximal and adjacent positional orientation in relation to the first lateral portion of the fourth elastic pivot hole.

15. The therapeutic assembly of claim 14, wherein:

said therapeutic assembly further comprises fifth, sixth, seventh and eighth pocket subassemblies, the fifth pocket subassembly being attached to the elastic support pattern in proximal and adjacent positional orientation in relation to the second lateral portion of the first elastic pivot hole, the sixth pocket subassembly being attached to the elastic support pattern in proximal and adjacent positional orientation in relation to the lateral portion of the third elastic pivot hole, the seventh pocket subassembly being attached to the elastic support pattern in proximal and adjacent positional orientation in relation to the posterior portion of the third elastic pivot hole, and the eighth pocket subassembly being attached to the elastic support pattern in proximal and adjacent positional orientation in relation to the second lateral portion of the fourth elastic pivot hole.

16. The therapeutic assembly of claim 15, wherein:

the first and fourth pocket subassemblies are integrally combined and structured as a first combined pocket subassembly, being attached to the elastic support pattern in proximal positional orientation in relation to the first lateral portion of the first elastic pivot hole and the first lateral portion of the fourth elastic pivot hole.

17. The therapeutic assembly of claim 16, wherein:

the fifth and eighth pocket subassemblies are integrally combined and structured as a second combined pocket subassembly, being attached to the elastic support pattern in proximal positional orientation in relation to the second lateral portion of the first pivot hole and the second lateral portion of the fourth elastic pivot hole.

18. The therapeutic assembly of claim 15, wherein:

the elastic support pattern further defines and has a second elastic fabriced layer having first and second surfaces, first and second end portions and first and second widthwise portions, each of said first and second widthwise portions having first, second and third subportions, said second elastic fabriced layer being fixedly attached to said first elastic fabriced layer such that its first surface is inboard of the second surface of the first elastic fabriced layer and slideable thereupon, the second surface of said second elastic fabriced layer being, as so attached, installable flush and immediately outboard of a surface of a treatment recipient.

19. The therapeutic assembly of claim 18, wherein:

the first pocket subassembly having first and second fluted pivot pockets, juxtaposed in series;

the second pocket subassembly having first, second and third fluted pivot pockets, juxtaposed in series;

the third pocket subassembly having first, second and third fluted pivot pockets, juxtaposed in series;

the fourth pocket subassembly having first, second and third fluted pivot pockets, juxtaposed in series;

the fifth pocket subassembly having first and second fluted pivot pockets, juxtaposed in series;

the sixth pocket subassembly having first, second and third fluted pivot pockets, juxtaposed in series;

the seventh pocket subassembly having first, second and third fluted pivot pockets, juxtaposed in series; and the eighth pocket subassembly having first, second and third fluted pivot pockets, juxtaposed in series;

each of the fluted pivot pockets defining and having first and second rounded entry channels.

20. The therapeutic assembly of claim 19, wherein:

the therapeutic assembly further comprises a ninth pocket subassembly, being attached to the elastic support pattern in proximal and adjacent positional orientation in relation to the posterior portion of the first elastic pivot hole.

21. The therapeutic assembly of claim 20, wherein:

each of the fluted pivot pockets is fabricated from a material selected from the group including fabric having threaded lengthwise biasing forces along longitudinal axes thereof and fabric having threaded widthwise and radially biasing forces along latitudinal axes thereof.

22. A therapeutic assembly for masked positional orientation and magnetic treatment, in interaction with areas of a head of a treatment recipient, said therapeutic assembly comprising:

an elastic support pattern, defining first, second, third and fourth elastic pivot holes, each positioned, respectively, to align proximally, when in a position for treatment use, with a nose, first eye, second eye and mouth area of a treatment recipient, the first elastic pivot hole having first lateral, second lateral, anterior and posterior portions, the second and third elastic pivot holes each having lateral, medial, inferior and superior portions, and the fourth elastic pivot hole having first lateral, second lateral, inferior and superior portions, and means for securing the elastic support pattern to a head of a treatment recipient;

a plurality of magnet components having, when so positioned, a magnetic differential thereof to attract and repel in relation to one another, each of the plurality of magnet components comprising a flexible and resilient, cylindrically-configured magnet having first and second ends, a circumferential surfacing therebetween, and a first cross-sectional portion and a second cross-sectional portion positionally oriented along a lengthwise axis between the first and second ends such that the first cross-sectional portion comprises part of the radial cross-sectional diameter of each of the plurality of magnet components and the second cross-sectional portion comprises the other part thereof, the first cross-sectional portion defining, magnetically, and having a positive pole charge and the second cross-sectional portion defining, magnetically, and having a negative pole charge, each of said plurality of magnet components further comprising a cylindrically-configured collar member, defining a lengthwise oriented lumen through and within which each cylindrically-configured magnet is slideably and retrievably installed and mounted; and means for removably mounting and pivotally positioning each of the plurality of magnet components in relation to one another, for selectively engaging the magnetic differential thereof to attract and repel in relation to one another, said means comprising first, second, third, fourth, fifth, sixth, seventh and eighth elastic-biasing pocket subassemblies; each of said elastic-biasing pocket subassemblies having a plurality of fluted pivot pockets each defining an installation channel and at least one installation opening generally, transversely adjacent thereto, and at least one rounded access groove generally parallel and adjacent to, and communicating with, the installation channel, each of the plurality of fluted pivot pockets of each elastic-biasing pocket subassembly being placed in positional alignment in series in relation to one another;

the first elastic-biasing pocket subassembly being attached to the elastic support pattern in proximal and adjacent positional orientation in relation to the lateral portion of the first elastic pivot hole, the second elastic-biasing pocket subassembly being attached to the elastic support pattern in proximal and adjacent positional orientation in relation to the lateral portion of the second elastic pivot hole, the third elastic-biasing pocket subassembly being attached to the elastic support pattern in proximal and adjacent positional orientation in relation to the superior portion of the second elastic pivot hole, the fourth elastic-biasing pocket subassembly being attached to the elastic support pattern in proximal and adjacent positional orientation in relation to the first lateral portion of the fourth elastic pivot hole, the fifth elastic-biasing pocket subassembly being attached to the elastic support pattern in proximal and adjacent positional orientation in relation to the second lateral portion of the first elastic pivot hole, the sixth elastic-biasing pocket subassembly being attached to the elastic support pattern in proximal and adjacent positional orientation in relation to the lateral portion of the third elastic pivot hole, the seventh elastic-biasing pocket subassembly being attached to the elastic support pattern in proximal and adjacent positional orientation in relation to the superior portion of the third elastic pivot hole, and the eighth elastic-biasing pocket subassembly being attached to the elastic support pattern in proximal and adjacent positional orientation in relation to the second lateral portion of the fourth elastic pivot hole;

each of the plurality of magnet components being mounted, respectively, in each of the fluted pivot pockets of each of the elastic-biasing pocket subassemblies, and selectively positionable, when so mounted, by selected access, respectively, through each of the rounded access grooves, to engage the magnetic differential thereof to attract and repel, thereby transmitting the magnetic differential and a resulting pulling and pushing force, respectively, through the elastic support pattern to adjacent areas of a head of a treatment recipient with which it interacts.

23. An improved cosmetic and therapeutic mask assembly, for use in interaction and relation to face and head areas of individual human and animal treatment subjects, said mask assembly comprising:

a flexible face-head mask pattern member having inboard and outboard surfaces, first and second end sections and first and second side sections, said flexible face-head mask pattern member defining a flexible sense-organ space having a perimeter, between its inboard and outboard surfaces, being generally disposed, centrally, between the first and second end sections thereof;

a plurality of magnet members, each having a substantially positively charged portion and a substantially negatively charged portion, and flexible, biasing and fluted pocket means for retrievably, positionally and pivotally mounting each of the plurality of magnet members in adjacent position to one another, for respective selected access and positioning, and alignment thereby, of the substantially positively charged portion and the substantially negatively charged portion, said flexible, biasing and fluted pocket means being mounted on the outboard surface of the flexible face-head mask pattern member in adjacent positional relation to the perimeter of the sense-organ space.

24. The improved cosmetic and therapeutic mask assembly of claim 23, further comprising means for installing and securing the mask assembly onto a treatment subject, for initially positioning the flexible sense-organ space and the adjacent flexible, biasing and fluted pocket means;

and wherein the perimeter of the sense-organ space defines first, second and third, generally trapezoidal sections communicating with one another, the first generally trapezoidal section having first and second linear lateral subsections and a, connecting, linear base subsection, the second and third generally trapezoidal sections, each having first and second parallel subsections and a, connecting lateral subsection, the first parallel subsection of the second generally trapezoidal section concurrently communicating with the first parallel subsection of the third generally trapezoidal subsection, the second parallel subsection of the second generally trapezoidal section communicating, generally transversely, with the first linear lateral subsection of the first generally trapezoidal section, and the second parallel subsection of the third generally trapezoidal section communicating, generally transversely, with the second linear lateral subsection of the first generally trapezoidal section;

and wherein said flexible, biasing and fluted pocket means comprises first, second, third, fourth, fifth and sixth pocket subassemblies, each having a medial perimeter and a lateral perimeter, and defining therebetween a plurality of fluted and biased pocket container members juxtaposed to one another in series.

25. The improved cosmetic and therapeutic mask assembly of claim 24, wherein:

the first pocket subassembly being attached to the flexible face-head mask pattern member in adjacent positional relation to the first linear lateral subsection of the first generally trapezoidal section, the second pocket subassembly being attached to the flexible face-head mask pattern member in adjacent positional relation to the lateral subsection of the second generally trapezoidal section, the third pocket subassembly being attached to the flexible face-head mask pattern member in adjacent positional relation to the first parallel subsection of the second generally trapezoidal section, the fourth pocket subassembly being attached to the flexible face-head mask pattern member in adjacent positional relation to the second linear lateral subsection of the first generally trapezoidal section, the fifth pocket subassembly being attached to the flexible face-head mask pattern member in adjacent positional relation to the lateral subsection of the third generally trapezoidal section, and the sixth pocket subassembly being attached to the flexible face-head mask pattern member in adjacent positional relation to the first parallel subsection of the third generally trapezoidal section.

26. The improved cosmetic and therapeutic mask assembly of claim 23, further comprising means for securing the mask assembly to a treatment subject, being attached to the flexible face-head mask pattern member in adjacent positional relation to the first end section and the first side section, of one side thereof, and the first end section and the second side section of the other side thereof, and wherein the perimeter of the sense-organ space defines a generally parabolic-configured section having a first arced-curve subsection, a second arced-curve subsection, and a, connecting, directrix subsection generally parallel and spaced from an imaginary directrix line formed in relation to the generally parabolic-configured section on imaginary Cartesian, x and y coordinate lines relating thereto.

* * * * *